US008124836B2

(12) United States Patent
Bate et al.

(10) Patent No.: US 8,124,836 B2
(45) Date of Patent: Feb. 28, 2012

(54) ***ZEA MAYS* ABA SIGNALING GENES AND METHODS OF USE**

(75) Inventors: Nicholas J Bate, Urbandale, IA (US); Xiping Niu, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 276 days.

(21) Appl. No.: 12/371,177

(22) Filed: Feb. 13, 2009

(65) Prior Publication Data

US 2009/0205067 A1 Aug. 13, 2009

Related U.S. Application Data

(60) Provisional application No. 61/028,256, filed on Feb. 13, 2008.

(51) Int. Cl.

| | |
|---|---|
| ***A01H 1/00*** | (2006.01) |
| ***A01H 5/00*** | (2006.01) |
| ***C12N 15/00*** | (2006.01) |
| ***C12N 15/04*** | (2006.01) |

(52) U.S. Cl. .................... 800/278; 800/298; 435/320.1; 435/410; 435/260

(58) Field of Classification Search ........................ None
See application file for complete search history.

(56) References Cited

U.S. PATENT DOCUMENTS 7,569,389 B2 * 8/2009 Feldmann et al. ............ 435/468

(Continued)

FOREIGN PATENT DOCUMENTS

WO 0136596 A2 5/2001

OTHER PUBLICATIONS

Meyer et al, Science, vol. 264, Jun. 3, 1994, pp. 1452-1455.*

(Continued)

*Primary Examiner* — Eileen B O Hara

(57) ABSTRACT

Compositions and methods for modulating abscisic acid (ABA) perception and signal transduction in developing seed are provided. The methods and compositions find use in increasing yield in plants, particularly under abiotic stress. Compositions comprise genetic constructs known to affect ABA sensitivity, particularly ABA biosynthetic mutants and fragments and variants thereof.

9 Claims, 3 Drawing Sheets

U.S. PATENT DOCUMENTS

2004/0148654 A1 * 7/2004 Helentjaris .................. 800/287

OTHER PUBLICATIONS

Yu, L-X and Setter, T.L.; "Comparative Transcriptional Profiling of Placenta and Endosperm in Developing Maize Kernels in Response to Water Deficit"; Plant Physiology (Feb. 2003) 131:568-582; American Society of Plant Biologists; Rockville, MD, US.

Sheen, J.; "Mutational analysis of protein phosphatase 2C involved in abscisic acid signal transduction in higher plants"; Proc. Natl. Acad. Sci. USA (Feb. 1998) 95:975-980; The National Academy of Sciences; Washington, DC, US.

Wang, Z., et al.; "Abscisic Acid Catabolism in Maize Kernels in Response to Water Deficit at Early Endosperm Development"; Annals of Botany (2002) 90:923-630; Annals of Botany Company; Oxford UK.

Lai, J., et al.; EMBL Database Number: BT017295; "*Zea mays* clone ELO0N0315F01.c mRNA sequence"; Oct. 28, 2004.

Collura, K., et al.; EMBL Database No. EE047848; "ZM_BFc0120N03.r ZM_BFc *Zea mays* cDNA clone ZM_BFc0120NO3 5', mRNA sequence"; Jul. 19, 2006.

Nakamura, S., et al.; "Mapping diploid wheat homologues of Arabidopsis seed ABA signaling genes and QTLs for seed dormancy"; Theor Appl Genet (2007) 114:1129-1139; Springer-Verlag; Berlin/Heidelberg, Germany.

Nishimura, N., et al.; "ABA-Hypersentative Germination1 encodes a protein phosphatase 2C, an essential component of abscisic acid signaling in Arabidopsis seed"; The Plant Journal (2007)50:935-949; Blackwell Publishing Ltd.; Oxford, UK.

Lorenzo, O., et al.; "A New Protein Phosphatase 2C (FsPP2C1) Induced by Abscisic Acid is Specifically Expressed in Dormant Beechnut Seeds"; Plant Physiology (Apr. 2001) 125:1949-1956; American Society of Plant Physiologists; Rockville, MD, US.

* cited by examiner

```
AtABI1-1    (1) -------------------------MEEVSPAIAGPFRPFSETQMDFTGIRLGKGYCNNQYSNQDSENGDLMVSLPETSSCSVSGSHGSESRKVLISRIN
ZM-ABI1     (1) MEDVVAVVASLSAPPAPAFSPAAAGLTLIAAAVADPIAAVVVGAMEGVSVPV-TVPPVRTASAVDDDALAPGEEGGDASLAGSPCSVVSDCSSVASADFE
Consensus   (1)                          L  IA AIA P        MD   I L         S  D D         D S      S  SD   V  A

AtABI1-1   (76) SPNLNMKESAAADIVVVDISAGDEINGSDITSEKKMISRTESRSLFEFKSVPLYGFTSICGRRPEMEDAVSTIPRFLQS-----SSGSMLDGR--FDPQS
ZM-ABI1   (100) GVGLCFFGAAAGAEGGPMVLEDSTASAATVEAEARVAAGG--RSVFAVDCVPLWGYTSICGRRPEMEDAVAIVPRFFDLPLWLLTGNAMVDGLDPMTFRL
Consensus (101)    L    AAAA      I       AA I AE KM A    RSLF    VPLWGFTSICGRRPEMEDAVA IPRF        S  AMLDG

AtABI1-1  (169) AAHFFGVYDGHDGSQVANYCRERMHLALAEEIAKEKPMLCDGDT----WLEKWKKALFNSFLRVDSEIES-----------------------VAPETVG
ZM-ABI1   (198) PAHFFGVYDGHGGAQVANYCRERLHVALLEQLSRIEETACAANLGDMEFKKQWEKVFVDSYARVDDEVGGNTMRGGGEEAGTSDAAMTLVPEPVAPETVG
Consensus (201)  AHFFGVYDGH GAQVANYCRERLHLAL E IAK     C A      F   W K    SF RVD EI                         VAPETVG

AtABI1-1  (242) STSVVAVVFPSHIFVANCGDSRAVLCRGKTALPLSVDHKPDREDEAARIEAAGGKVIQWNGARVFGVLAMSRSIGDRYLKPSIIPDPEVIAVKRVKEDDC
ZM-ABI1   (298) STAVVAVICSSHIIVSNCGDSRAVLCRGKQPVPLSVDHKPNREDEYARIEAEGGKVIQWNGYRVFGVLAMSRSIGDRYLKPWIIPVPEVTIVPRAKDDEC
Consensus (301) STAVVAVI  SHI VANCGDSRAVLCRGK  LPLSVDHKP REDE ARIEA GGKVIQWNG RVFGVLAMSRSIGDRYLKP IIP PEVT V R KDDDC

AtABI1-1  (342) LILASDGVWDVMTDEEACEMARKRILLWHKKNAVAGDASLLADERRKEGKDPAAMSAAEYLSKLAIQRGSKDNISVVVVDLKPRRKLKSKPLN
ZM-ABI1   (398) LILASDGLWDVMSNEEVCEIARKRILLWHKKNSTSSSS----APRVGDSADSAAQAATECLSKLALQKGSKDNITVVVVDLKAQRKFKSKT--
Consensus (401) LILASDGLWDVMS EE CEIARKRILLWHKKNA A  A      R  D  D AA AA E LSKLAIQKGSKDNISVVVVDLK  RK KSK
```

Alignment of Arabidopsis ABI1 (AT-ABI1; SEQ ID NO: 2) with maize ABI1 (ZM-ABI1; SEQ ID NO: 4). Consensus shown is SEQ ID NO: 14.

FIGURE 2 p0005.cbmfd76r.GSS: Gene Structure of ZmABI1 from BMS cells

*ZEA MAYS* ABA SIGNALING GENES AND METHODS OF USE

CROSS REFERENCE

This utility application claims the benefit of U.S. Provisional Application No. 61/028,256, filed Feb. 13, 2008; which is incorporated herein by reference.

FIELD OF THE INVENTION

The present invention comprises compositions and methods for the genetic modification of plants, particularly for modulating plant response to abscisic acid.

BACKGROUND OF THE INVENTION

Abscisic acid (ABA) is a phytohormone that plays an essential regulatory role in a variety of physiological processes, including embryo development, seed dormancy, transpiration, and adaptation to environmental stresses. ABA regulates many agronomically important aspects of plant development including synthesis of seed storage proteins and lipids as well as regulation of stomatal closure. The analysis of ABA-responsive promoters has revealed a diversity of potential cis-acting regulatory elements.

Mutations in genes impacting ABA biosynthesis and signaling are known in several plant species. See, for example, Leung and Giraudat, (1998) *Annu. Rev. Plant Physiol. Plant Mol. Biol.* 49:199-222, and the references cited therein. In *Arabidopsis*, a number of genetically distinct *Arabidopsis* acid-insensitive loci have been identified. These mutants were selected based on the ability of seeds to germinate in the presence of inhibitory concentrations of ABA. The mutations have also been shown to affect several additional aspects of seed development, including accumulation of storage proteins and lipids, chlorophyll breakdown, desiccation tolerance, and embryonic maturation. In addition, ABA-mediated growth control is a fundamental response of plants to adverse environmental conditions. Methods are needed to modulate the response of plants to ABA, particularly for mitigating effects of abiotic stress on vegetative and/or reproductive growth in order to maintain or increase yield.

SUMMARY OF THE INVENTION

Compositions and methods for increasing yield in plants, particularly seed plants, are provided. The methods involve modulating abscisic acid (ABA) perception and signal transduction to protect plants against the detrimental effects of stress and adverse environmental conditions. Compositions comprise genetic constructs which affect ABA sensitivity in a plant or plant cell. Of particular interest are ABA-associated sequences. Such sequences include mutants, fragments and variants, as well as antisense nucleotide sequences, for genes involved in the perception and signal transduction of ABA. The DNA sequences may be provided in constructs providing temporal, developmental, and/or tissue specificity. Compositions are useful in methods for increasing yield of plants under stress, particularly abiotic stress. In this manner, detrimental effects of ABA on plant growth and/or yield are ablated. Transformed plants, plant cells, tissues, and seeds are additionally provided.

BRIEF DESCRIPTION OF THE FIGURES

FIG. 2 is an alignment of *Arabidopsis* and *Zea mays* ABI1 proteins.

BRIEF DESCRIPTION OF THE SEQUENCES

Figure 3:
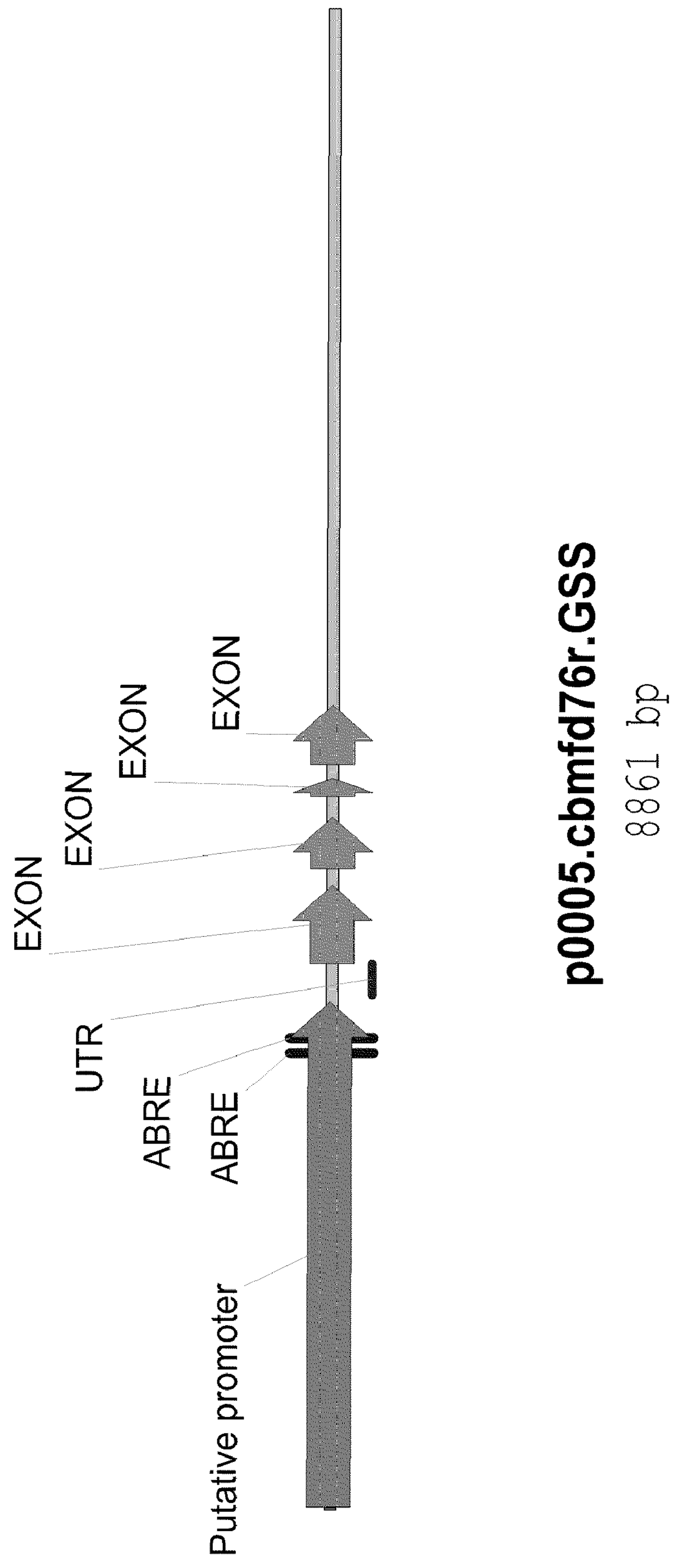
FIG. 3 provides information about the maize gene identified at SEQ ID NO: 13.

*Arabidopsis* ABI1 sequences are provided in SEQ ID NO: 1 and 2. Maize ABI1 nucleic acid and amino acid sequences are provided in SEQ ID NO: 3 and 4. Partial ZmABI1 homologues A, B and C are provided in SEQ ID NOS: 5, 6 and 7, respectively. ZmABI-GF and a homologue are provided in SEQ ID NOS: 8, and 9, respectively, and the amino acid sequence of ZmABI-GF is provided at SEQ ID NO: 10. SEQ ID NO: 11 and 12 are a mutant ZmABI1 sequence further described herein. SEQ ID NO: 13 is the genomic sequence of an ABA-inducible gene with an ABRE (ABA responsive element) in the promoter region; see also, FIG. 3.

DETAILED DESCRIPTION OF THE INVENTION

Methods for modulating plant response to abscisic acid (ABA) are provided. In certain embodiments, crop yield is maintained by ablating the detrimental effects of ABA on seed development. In particular, the invention comprises compositions and methods for disrupting or delaying ABA signaling or function. The compositions and methods are useful for disrupting or delaying ABA function or effect in a tissue-preferred and/or developmentally-preferred manner to insulate vegetative and/or reproductive tissue from stress and adverse environmental conditions. This may advantageously alter the developmental time frame of certain tissues so as to minimize effects of abiotic stress. For example, the timing of certain aspects of endosperm development may be altered to avoid negative impacts of abiotic stress.

For purposes of the invention, "seed development" includes, without limitation, the initiation and development of reproductive tissue, endosperm development, and seed maturation.

ABA is involved in many physiological and developmental processes throughout the life cycle of plants, including seed dormancy; adaptation to abiotic environmental stresses such as cold, drought, salinity, etc.; accumulation of nutritive reserves; acquisition of desiccation tolerance; stomatal closure; and the like. ABA mediates plant adaptation to environmental cues such as desiccation, cold, salt stress, and other stresses, and acts as a negative growth regulator. Generally, ABA imposes bimodal negative growth control by regulating the potential of the cell to enlarge, possibly by turgor control, and by inducing mitotic growth arrest.

Certain embodiments of the invention comprise controlling or modulating the plant response to the ABA signal. By "modulating" is intended the up-regulation or down-regulation of the plant response to ABA. For purposes of the invention, modulation is generally down-regulation of plant response by the disruption of ABA synthesis and/or the disruption of the perception and/or signal transduction of ABA. It is recognized that total disruption of ABA function in plants is not practical, as ABA performs many useful roles in plant development. Certain embodiments of the invention disrupt the effects of ABA at the site of the eventual effect, e.g., flowers and seeds. In this manner, disruption of ABA perception or its signal transduction provides an effective strategy in insulating female reproductive tissue growth from stress.

Environmental stresses at or just after the time of fertilization inhibit early events in establishment of sink capacity and can decrease yield. In cereals, for example, the endosperm is the major source of stored reserves within the mature seed. Storage capacity is established during an early stage of seed development. Recognizing ABA involvement in early plant responses to stress, certain embodiments of the present invention comprise ablation of the detrimental effects of ABA on the developing seed, improving the nature and quantity of seed and seed products, particularly cereals and grains. See, Mambelli and Setter, (1998) *Physiologia Plantarum* 104: 266-72 and Tuberosa, et al., (1998) *Theor. Appl. Genet.* 7:44-55.

As indicated, certain embodiments of the invention comprise introducing, into a target plant, sequences that modulate ABA perception and signal transduction. By "sequences that modulate ABA perception and signal transduction" and "sequences involved in the perception and signal transduction of ABA" are intended genes and their mutant forms that disrupt ABA synthesis or its perception and signal transduction. These mutants, genes, and sequences that disrupt ABA synthesis or its perception or signal transduction, are also called "ABA-associated sequences" herein. Such sequences include, but are not limited to, ABA-insensitive and hypersensitive mutants or antisense sequences corresponding to the mutant or wild-type genes. ABA mutants are known in the art and include abi1-5, era1-3 (Cutler, et al., (1996) *Science* 273:1239-41), gca1/8 (Benning, et al., (1996) *Proc. Workshop Abscisic Acid Signal Transduction in Arabidopsis*, Madrid, p. 34), axr2 (Wilson, et al., (1990) *Mol. Gen. Genet.* 222:377-83), jar1 (Staswick, et al., (1992) *Proc. Natl. Acad. Sci. USA* 89:6837-40), jin4 (Berger, et al., (1996) *Plant Physiol.* 111:525-31), bri1 (Clouse, et al., (1996) *Plant Physiol.* 111:671-78) (*Hordeum vulgare*); aba1 (Bitoun, et al., (1990) *Mol. Gen. Genet.* 220:234-39 and Leydecker, et al., (1995) *Plant Physiol.* 107:1427-31) (*Nicotiana plumbaginifolia*); and the like. These and other ABA-associated mutants can be used in the practice of the invention.

By "corresponding" to a gene or sequence is intended that the sequence is capable of hybridizing to the gene or sequence to the extent necessary to disrupt transcription. It is recognized that depending on the ABA-associated sequence utilized in the invention, the coding sequence or the antisense sequence may be preferred. However, the coding sequence may also be used to co-suppress expression of the target gene. For example, one strategy includes expression of a mutant abi1 gene with an early kernel/embryo promoter to dominantly disrupt ABA action in tissues at early seed-forming stages. Such an approach would not disrupt the later required ABA function in seed maturation. Thus, as described more fully below, several candidate gene targets are available to be coupled with promoters with various expression patterns to provide increased yield stability in the face of abiotic stress.

*Arabidopsis* ABA-insensitive, ABI, mutants are available. Such mutants have pleiotropic defects in seed development, including decreased sensitivity to ABA inhibition of germination in altered seed-specific gene expression. See, Finkelstein, et al., (1998) *The Plant Cell* 10:1043-1045; Leung, et al., (1994) *Science* 264:1448-1452; Leung (1997) *Plant Cell* 9:759-771; Giraudat, et al., (1992) *Plant Cel*14:1251-1261; Myer, et al., (1994) *Science* 264:1452-1455; Koornneef, et al., (1989) *Plant Physiol.* 90:463-469; Nambara, et al., (1992) *Plant J.* 2:435-441; Finkelstein and Somerville, (1990) *Plant Physiol.* 94:1172-1179; Leung and Giraudat, (1998) *Annu. Rev. Plant Physiol. Plant Mol. Biol.* 49:199-222; Robinson and Hill, (1999) *Plant, Cell and Environment* 22:117-123; and Rodriguez, et al., (1998) *FEBS Letters* 421:185-190, and the references cited therein, all of which are herein incorporated by reference. Other ABA-associated mutants include bri1 from *Arabidopsis thaliana*, the sequence of which can be found in Genbank Accession Number AF017056 and Li, et al., (1997) *Cell* 90:929-938, both of which are herein incorporated by reference.

An abi mutant of interest includes, for example, *Arabidopsis* abi1, a dominant mutation in the structural part of the ABI1 gene, which encodes a protein phosphatase 2C (PP2C). This mutation comprises a nucleic base transition from guanine to adenine which changes the DNA sequence GGC to GAC, thus causing the wild type glycine residue at amino acid position 180 of SEQ ID NO: 2 to be replaced with aspartic acid (referred to as G180D; Meyer, et al., (1994) *Science* 264:1452-1455).

The nucleic acid and amino acid sequences of wild type *Arabidopsis* ABI1 are set forth in SEQ ID NOS: 1-2. The nucleic acid and amino acid sequences of wild-type *Zea mays* ABI1, also a PP2C, are set forth in SEQ ID NOS: 3-4. This maize gene has high homology to an ABI1 gene from Indica rice. Partial sequences for three additional closely-related maize homologues are provided at SEQ ID NOS: 5, 6 and 7. SEQ ID NOS: 11 and 12 represent a maize mutant similar to the *Arabidopsis* G180D mutant. In the case of maize, the coding sequence is altered to change a glycine at position 193 to aspartic acid. A 16-residue deletion in the N-terminal portion of the mutant (corresponding to amino acids 22 to 37 in the wild-type protein) does not appear to affect activity.

A second ZmABI1 gene, isolated from GaspeFlint and having high homology to an ABI gene from Japonica rice, is provided at SEQ ID NOS: 8 and 10 as ZmABI1-GF. A further maize homologue of ZmABI-GF is provided at SEQ ID NO: 9.

Such mutants listed above are designated "ABA-associated mutants." By "ABA-associated mutants" is intended genes and sequences which disrupt ABA signaling and/or perception in a plant. Utilizing the maize ABI1 sequence above, related sequences from other plants, including cereals, can be isolated. In some instances, it may be beneficial to use the ABA-associated sequence that corresponds to a sequence from the target plant of interest. For example, for use in maize, the maize homolog of the ABA-associated sequence, or a sequence corresponding to the maize homolog, may be preferred.

Certain embodiments of the invention utilize the ABA-associated sequences to control the plant response to ABA. Generally, it will be beneficial to block ABA signaling or perception in selected tissues, such as female reproductive tissues, to prevent a loss of yield. Utilizing the ABA-associated sequences, coding sequences, and antisense sequences, the expression and perception of ABA in a plant can be controlled. As described in more detail below, such sequences can be introduced into plants of interest by recombinant methods as well as by traditional breeding methods.

The nucleotide sequences of the invention can be used to isolate corresponding sequences from other organisms, particularly other plants, more particularly cereals. In this manner, methods such as PCR, hybridization, and the like can be used to identify such sequences based on their sequence homology to the ABA-associated sequences known in the art. Sequences may be isolated based on their sequence identity to the entire ABA-associated sequence or to fragments thereof.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen plant. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the ABA-associated sequences of the invention. Methods for preparation of probes for hybridization and for construction of cDNA and genomic libraries are generally known in the art and are disclosed in Sambrook, et al., (1989) *Molecular Cloning: A Library Manual* (2d ed., Cold Spring Harbor Laboratory Press, Plainview, N.Y.).

For example, an entire ABA-associated sequence, or one or more portions thereof, may be used as a probe capable of specifically hybridizing to corresponding sequences and messenger RNAs. To achieve specific hybridization under a variety of conditions, such probes include sequences that are unique among the sequences of interest and are preferably at least about 10 nucleotides in length. Such probes may be used to amplify corresponding sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Duration of hybridization is generally less than about 24 hours, usually about 4 to 12. Stringent conditions may also be achieved with the addition of destabilizing agents such as formamide. Exemplary low stringency conditions include hybridization with a buffer solution of 30 to 34% formamide, 1 M NaCl, 1% SDS (sodium dodecyl sulphate) at 37° C., and a wash in 1× to 2×SSC (20×SSC=2.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution and L is the length of the hybrid in base pairs. The $T_m$ is the temperature (under defined ionic strength and pH) at which 50% of a complementary target sequence hybridizes to a perfect matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel, et al., eds. (1995) *Current Protocols in Molecular Biology, Chapter* 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

Thus, isolated "corresponding ABA-associated sequences" that modulate the plant response to ABA and which hybridize under stringent conditions to the ABA-associated sequences disclosed herein, or to fragments thereof, are encompassed by the present invention. Such sequences will be at least about 40% to 50% homologous, about 60%, 65% or 70% homologous, and even at least about 75%, 80%, 85%, 90%, 91%, 92%, 93%, 94%, 95%, 96%, 97%, 98%, 99% or more homologous with the disclosed sequences. That is, the sequence identity of sequences may range, sharing at least about 40% to 50%, about 60%, 65% or 70%, and even at least about 75%, 80%, 85%, 90%, 91%, 92%, 93%, 94%, 95%, 96%, 97%, 98%, 99% or more sequence identity.

The ABA-associated sequences of the invention can be utilized with tissue or developmental-specific promoters to disrupt ABA function in a tissue or a developmentally specific manner. Promoters of particular interest include seed-preferred promoters, particularly early kernel/embryo promoters and late kernel/embryo promoters.

Kernel development post-pollination is divided into approximately three primary phases. The lag phase of kernel growth occurs from about 0 to 10-12 days after pollination (DAP). During this phase the kernel is not growing significantly in mass, but rather important events are being carried out that will determine kernel vitality (i.e., number of cells). The linear grain fill stage begins at about 10-12 DAP and continues to about 40 DAP. During this stage of kernel development, the kernel attains almost all of its final mass and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "Early kernel/embryo promoters" are promoters that drive expression principally during the lag phase of development (i.e., from about 0 to about 12 DAP). "Late kernel/embryo promoters", as defined herein, drive expression principally from about 12 DAP through maturation. There may be some overlap in the window of expression. The choice of the promoter will depend on the ABA associated sequence utilized and the phenotype desired.

Early kernel/embryo promoters include, for example, cim1, a pollen and whole kernel specific promoter that is active 5 DAP. See, for example, WO 00/11177, which is herein incorporated by reference. Other early kernel/embryo promoters include the seed-preferred promoters end1, which is active 7-10 DAP, and end2, which is active 9-14 DAP in the whole kernel and active 10 DAP in the endosperm and pericarp. See, for example, WO 00/12733, herein incorporated by reference. Additional early kernel/embryo promoters that find use in certain methods of the present invention include the seed-preferred promoter ltp2, U.S. Pat. No. 5,525,716; maize Zm40 promoter, U.S. Pat. No. 6,403,862; maize nuc1c, U.S. Pat. No. 6,407,315; maize ckx1-2 promoter, U.S. Pat. No. 6,921,815 and US Patent Application Publication Number 2006/0037103; maize lec1 promoter, U.S. Pat. No. 7,122, 658; maize ESR promoter, U.S. Pat. No. 7,276,596; maize ZAP promoter, US Patent Application Publication Numbers 20040025206 and 20070136891; maize promoter eep1, US Patent Application Publication Number 20070169226; and maize promoter ADF4, U.S. Patent Application No. 60/963, 878 filed 7 Aug. 2007. These promoters drive expression in developing seed tissues.

Such early kernel/embryo promoters can be used with genes or mutants in the perception/signal transduction pathway for ABA. In this manner, mutant genes such as abi1 or abi2 operably linked to an early kernel/embryo promoter would dominantly disrupt ABA action in the targeted tissues but not alter the later required ABA function in seed maturation. Alternatively, an early kernel/embryo promoter can be operably linked to a wild type (co-suppression) or antisense nucleotide sequence of an ABA associated sequence. The early kernel/embryo promoter would be utilized to disrupt ABA action in tissue prior to seed maturation.

By "introducing" sequences that modulate ABA perception and signal transduction into a target plant is encompassed any means for incorporating the sequence of interest into the target plant. Such means include conventional breeding methods, genetic transformation methods, or other such means as may be available. The methods of the invention do not depend on a particular method for introducing a nucleotide construct to a plant, only that the nucleotide construct gains access to the interior of at least one cell of the plant. By "stable transformation" is intended that the nucleotide construct introduced into a plant integrates into the genome of the plant and is capable of being inherited by progeny thereof.

When downregulation is desired, antisense constructions complementary to at least a portion of the messenger RNA (mRNA) for the ABA-associated sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisensed sequence may be used. Furthermore, portions of the antisense nucleotides may be used to disrupt the expression of the target gene. Generally, sequences of at least 50 nucleotides, 100 nucleotides, 200 nucleotides or greater may be used.

Methods for suppressing gene expression in plants using nucleotide sequences in the sense orientation are also known in the art. The methods generally involve transforming plants with a DNA construct comprising a promoter that drives expression in a plant operably linked to at least a portion of a nucleotide sequence that corresponds to the transcript of the endogenous gene (i.e., an ABA-associated sequence). Typically, such a nucleotide sequence has substantial sequence identity to the sequence of the transcript of the endogenous gene, preferably greater than about 65% sequence identity, and often greater than about 85% sequence identity, such as about 95% sequence identity. See, U.S. Pat. Nos. 5,283,184 and 5,034,323, all of which are herein incorporated by reference.

It is recognized that fragments and/or variants of the ABA-associated genes can be utilized in the invention. Fragments and variants of the ABA-associated nucleotide sequences and proteins encoded thereby are thus encompassed by the present invention. By "fragment" is intended a portion of the nucleotide sequence or a portion of the amino acid sequence and hence of the protein encoded thereby. Fragments of a nucleotide sequence may encode protein fragments that retain the biological activity of the native protein and hence act to modulate responses to ABA. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, or about 100 nucleotides, up to the full-length nucleotide sequence of the invention.

By "variants" is intended substantially similar sequences. For nucleotide sequences, naturally-occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 50%, 60%, 65%, 70%, generally at least about 75%, 80%, 85%, often at least about 90%, 92%, 94%, 95%, 96%, 97%, or even about 98%, 99% or more sequence identity to that particular nucleotide sequence as determined by sequence alignment programs described elsewhere herein.

Methods of alignment of sequences for comparison are well known in the art. Thus, determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith, et al., (1981) *Adv. Appl. Math.* 2:482; the homology alignment algorithm of Needleman and Wunsch, (1970) *J. Mol. Biol.* 48:443-453; the search-for-similarity-method of Pearson and Lipman, (1988) *Proc. Natl. Acad. Sci.* 85:2444-2448; the algorithm of Karlin and Altschul, (1990) *Proc. Natl. Acad. Sci. USA* 87:2264, modified as in Karlin and Altschul, (1993) *Proc. Natl. Acad. Sci. USA* 90:5873-5877.

Computer implementation of these mathematical algorithms can be utilized for comparison of sequences to determine sequence identity. Such implementations include, but are not limited to: CLUSTAL in PC/Gene program (available from Intelligenetics, Mountain View, Calif.); the ALIGN program (Version 2.0) and GAP, BESTFIT, BLAST, FASTA, and TFASTA in the Wisconsin Package®, Version 8 or Version 10 (available from Accelrys® Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-165; and Pearson, et al., (1994) *Meth. Mol. Biol.* 24:307-331. The ALIGN program is based on the algorithm of Myers and Miller, (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Atschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See the website of the National Center for Biotechnology Information. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleham and Wunsch, (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creating penalty number of matches for each gap it inserts. If a gap extension penalty greater than zero is chosen, GAP must, in addition, make a profit for each gap inserted of the length of the gap times the gap extension penalty. Default gap creation penalty values and gap extension values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 67 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. Methods for mutagenesis and nucleotide sequence alterations are well known in the art. See, for example, Kunkel, (1985) *Proc. Natl. Acad. Sci. USA* 82:488-492; Kunkel, et al., (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological actively of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired activity. Obviously, the mutations that will be made in the DNA encoding the variant must not place the sequence out of reading frame and preferably will not create complementary regions that could produce secondary mRNA structure. See, EP Patent Application Publication Number 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant nucleotide sequences and proteins also encompass sequences and proteins derived from a mutagenic and recombinogenic procedure such as DNA shuffling. With such a procedure, one or more different ABA-associated coding sequences can be manipulated to create a new ABA-associated protein possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1988) *Nature* 391:288-291; and U.S. Pat. Nos. 5,605,793 and 5,837,458.

The ABA-associated sequences of the invention are provided in expression cassettes for expression in the plant of interest. The cassette will include 5' and 3' regulatory sequence operably linked to an ABA-associated sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the sequence of interest to be under the transcriptional regulation of the regulatory regions. The expression cassette may additionally contain selectable marker genes.

The expression cassette will include in the 5'-3' direction of transcription, a transcriptional and translational initiation region, a DNA sequence of the invention, and a transcriptional and translational termination region functional in plants. The transcriptional initiation region, the promoter, may be native or foreign to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence. While it may be preferable to express the sequences using heterologous promoters, the native promoter sequences may be used. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nonpaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acid Res.* 15:9627-9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831 and 5,436,391, and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, et al., (1989) *PNAS USA* 86:6126-6130); potyvirus leaders, for example, TEV leader (Tobacco Etch Virus) (Allison, et al., (1986); MDMV leader (Maize Dwarf Mosaic Virus); *Virology* 154:9-20), and human immunoglobulin heavy-chain protein (BiP), (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA, ed. Cech* (Liss, New York), pp. 237-256); and maize chlorotic mottle virus leader (MCMV) (Lommel, et al., (1991) *Virology* 81:382-385). See also, Della-Cioppa, et al., (1987) *Plant Physiol.* 84:965-968. Other methods known to enhance translation can also be utilized, for example, introns, and the like.

In preparing the expression cassette, the various DNA fragments may be manipulated, so as to provide for the DNA sequence in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Transformation protocols as well as protocols for introducing nucleotide sequences into plants may vary depending on the type of plant or plant cell, e.g., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606, *Agrobacterium*-mediated transformation (Townsend, et al., U.S. Pat. No. 5,981,840), direct gene transfer (Paszkowski, et al., (1984) *EMBO J.* 3:2717-2722), and ballistic particle acceleration (see, for example, Sanford, et al., U.S. Pat. No. 4,945,050; Tomes, et al., (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe, et al., (1988) *Biotechnology* 6:923-926). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Sci. USA* 85:4305-4309 (maize); Klein, et al., (1988) *BioTechnology* 6:559-563 (maize); Tomes, U.S. Pat. No. 5,240,855; Buising, et al., U.S. Pat. Nos. 5,322,783 and 5,324,646; Tomes, et al., (1995) "Direct DNA Transfer into Intact Plant Cells via Microprojectile Bombardment," in *Plant Cell, Tissue, and Organ Culture: Fundamental Methods*, ed. Gamborg (Sprinter-Verlag, Berlin) (maize); Klein, et al., (1988) *Plant Physiol.* 91:440-444 (maize); Fromm, et al., (1990) *Biotechnology* 8:833-839 (maize); Hooykaas-Van Solgteren, et al., (1984) *Nature* (London) 311:763-764; Bowen, et al., U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler et al. (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and a resulting plant having acceptable expression of the desired phenotypic characteristic identified. Two or more generations may be grown to ensure that expression of the desired phenotypic characteristic is stably maintained and inherited and then seeds harvested to ensure reliable expression of the desired phenotypic characteristics has been achieved.

Certain embodiments of the present invention comprise transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setara italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gssypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*) tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing certain embodiments of the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiate*); Douglas-fir (*Pseudotsuga menziesii*); Western hemlock (*Tsuga Canadensis*); Sitka spruce (*Picea galuca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The following examples are offered by way of illustration and not by way of limitation.

EXPERIMENTAL

Transformation and Regeneration of Transgenic Plants

Example 1

Biolistic Transformation and Regeneration of Transgenic Maize Plants

Immature maize embryos from greenhouse donor plants are bombarded with a plasmid containing the maize ABI1 sequence, or the sequence of a maize abi1 mutant based on the *Arabidopsis* abi1 G180D mutant, operably linked to an early kernel/embryo promoter, plus a plasmid containing the selectable marker gene PAT (Wohlleben, et al., (1988) *Gene* 70:25-37) that confers resistance to the herbicide Bialaphos. Transformation is performed as follows. All media recipes are below.

Preparation of Target Tissue

The ears are surface sterilized in 30% Clorox® bleach plus 0.5% Micro detergent for 20 minutes, and rinsed two times in sterile water. The immature embryos are excised and placed embryo axis side down (scutellum side up), 25 embryos per plate, on 560Y medium for 4 hours and then aligned with the 2.5-cm target zone in preparation for bombardment.

Preparation of DNA

A plasmid vector is made which comprises the mutant maize abi1 sequence operably linked to an early kernel/embryo promoter. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pallet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every two weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/12, 4-D, and 2.88 g/l L-proline (brought to volume with D-I $H_2O$ following adjustment to pH 5.8 with KOH); 2.0 g/l Gelrite® (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustments to pH 5.8 with KOH); 3.0 g/l Gelrite® (added after bring to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/1 myo-inositol, 0.3 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite® (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$, 0.1/l myo-inositol, and 40.0 g/l sucrose (brought to volume with polished D-I $H_2O$ after adjusting pH to 5.6); and 6 g/l Bacto™-agar (added after bringing to volume with polished D-I $H_2O$), sterilized and cooled to 60° C.

Example 2

*Agrobacterium*-Mediated Transformation of Maize

For *Agrobacterium*-mediated transformation of maize with a mutant maize abi1 sequence operably linked to an early kernel/embryo promoter, preferably the method of Zhao is employed (U.S. Pat. No. 5,981,840, and PCT Patent Publication WO98/32326; the contents of which are hereby incorporated by reference). Briefly, immature embryos are isolated from maize and the embryos contacted with a suspension of *Agrobacterium*, where the bacteria are capable of transferring the abi1 sequence operably linked to an early kernel/embryo promoter to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). The immature embryos may be cultured on solid medium following the infection step. Following this co-cultivation period an optional "resting" step is contemplated. In this resting step, the embryos are incubated in the presence of at last one antibiotic known to inhibit the growth of *Agrobacterium* without the addition of a selective agent for plant transformants (step 3: resting step). The immature embryos may be cultured on solid medium with antibiotic, but without a selecting agent, for elimination of *Agrobacterium* and for a resting phase for the infected cells. Next, the inoculated embryos are cultured on medium containing a selective agent and growing transformed callus is recovered (step 4: the selection step). The immature embryos may be cultured on solid medium with a selective agent resulting in the selective growth of transformed cells. The callus is then regenerated into plants (step 5: the regeneration step), and preferably calli grown on selective medium are cultured on solid medium to regenerate the plants.

Example 3

Soybean Embryo Transformation

Soybean embryos are bombarded with a plasmid containing the mutant maize abi1 nucleotide sequence operably linked to an early embryo/kernel promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-13, U.S. Pat. No. 4,945,050). A DuPont Biolistic PDS 1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188), and the 3' region of the nopaline synthase gene from the T-DNA of the Ti plasmid of *Agrobacterium tumefaciens*. The expression cassette comprising the mutant abi1 nucleotide sequence operably linked to an early kernel/embryo promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches of mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 4

Sunflower Meristem Tissue Transformation

Sunflower meristem tissues are transformed with an expression cassette containing a mutant maize abi1 sequence operably linked to an early kernel/embryo promoter as follows (see also, European Patent Number EP 0486233, herein incorporated by reference, and Malone-Schoneberg, et al. (1994) *Plant Science* 103:199-207). Mature sunflower seed (*Helianthus annuus* L.) are dehulled using a single wheat-head thresher. Seeds are surface sterilized for 30 minutes in a 20% Clorox® bleach solution with the addition of two drops of Tween™ 20 per 50 ml of solution. The seeds are rinsed twice with sterile distilled water.

Split embryonic axis explants are prepared by a modification of procedures described by Schrammeijer, et al. (Schrammeijer, et al., (1990) *Plant Cell Rep.* 9:55-60). Seeds are imbibed in distilled water for 60 minutes following the surface sterilization procedure. The cotyledons of each are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant* 15:473-497), Shepard's vitamin additions (Shepard (1980) in *Emergent Techniques for the Genetic Improvement of Crops* (University of Minnesota Press, St. Paul, Minn.), 40 mg/l indole-3-acetic acid (IAA), 0.1 mg/l gibberellic acid ($GA_3$), pH 5.6, and 8 g/l Phytagar (Invitrogen, Carlsbad, Calif.).

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 9.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ABI3 gene operably linked to an early kernel/embryo promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bacto® peptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced sheets suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for modulation in the plant response to ABA.

NPTII-positive shoots are grated to Pioneer® hybrid 6440 in vitro-grown sunflower seedling rootstock. Surface sterilized seeds are germinated in 48-0 medium (half-strength Murashige and Skoog salts, 0.5% sucrose, 0.3% Gelrite®, pH5.6) and grown under conditions described for explant culture. The upper portion of the seedling is removed, a 1 cm vertical slice is made in the hypocotyl, and the transformed shoot inserted into the cut. The entire area is wrapped with Parafilm® to secure the shoot. Grafted plants can be transferred to soil following one week of in vitro culture. Grafts in the soil are maintained under high humidity conditions followed by a slow acclimatization to the greenhouse environment. Transformed sectors of $T_0$ plants (parental generation) maturing in the greenhouse are identified by, for example, NPTII ELISA of leaf extracts while transgenic seeds harvested from NPTII-positive $T_0$ plants are identified by assaying for modulation in the plant response to ABA.

Example 5

Cloning and Gene Characterization of ZmABI1

Sequences putatively representing ABI1 genes in maize were initially identified by an in silico search of proprietary maize EST and GSS databases using known *Arabidopsis* and rice ABI1 coding sequences. Candidate ESTs, were selected based on protein-level homology to the reference sequences and consideration of the library from which the candidate sequence originated.

Based on the candidate EST sequences, primers were created and used to screen a proprietary maize BAC library. Super-pools identified were further screened with appropriate primers to identify specific BAC clones comprising the ESTs.

In each case, touchdown PCR was performed (GeneAmp® PCR System 9700, Applied Biosystems), using the following cycling parameters: 94° C. for 3 min (one cycle), 94° C. for 1 min, 55° C. for 1 min and 72° C. for 1 min 30s, (35 cycles), 72° C. for 7 min, and termination at 4° C. Pfu Ultra Hotstart™ DNA polymerase (Stratagene) was used for its very low average error rate (less than 0.5% per 500-bp fragment amplified).

Maize insert DNA was isolated from the BAC clones and digested for Southern blot confirmation using a candidate EST clone as a probe. BAC fragments were subcloned into pBluescript® (Stratagene Inc., La Jolla, Calif.). White colonies were grown in LB medium and transferred onto a membrane using a dot-blot procedure. After denaturation the membrane was probed with a candidate EST clone. Positive clones were identified and sequenced.

Example 6

Characterization of Maize ABI Candidate Genes

To further characterize the isolated maize ABI1 genes, Lynx MPSS mRNA profiling was conducted (see, Brenner, et al., (2000) *Nature Biotechnology* 18:630-634; Brenner, et al., (2000) *PNAS* 97:1665-1670). Results are summarized in Table 1.

Example 7

Effect of ABI1 Modulation

Constitutive over-expression of the maize dominant mutant described herein (SEQ ID NO: 11) results in leaf firing and loss of vigor consistent with strong ABA insensitivity. This wilty phenotype is similar to the phenotype of ABA-biosynthetic mutants of maize.

In contrast, transgenic plants expressing the same mutant under the control of an early kernel/embryo promoter are healthy and do not display the wilty phenotype.

Figure 1:
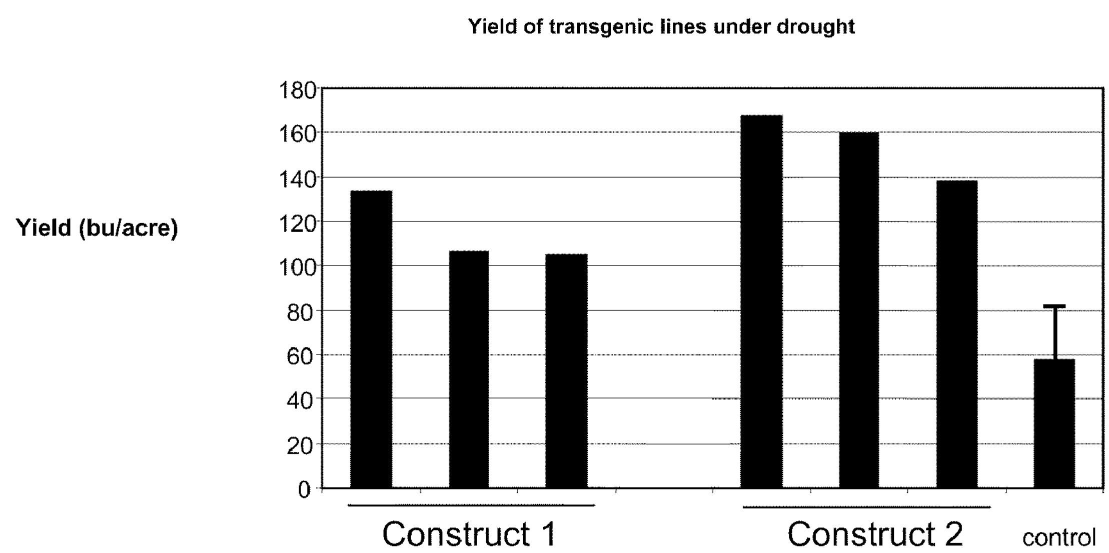
FIG. 1 presents yield data for ABI1 transgenic maize as described further in Example 7.

Transgenic maize plants expressing the maize ABI1-G180D dominant mutation (SEQ ID NO: 11) under the control of either of two early kernel promoters were grown under managed water stress conditions in Woodland, Calif. Results for three transgenic events of each construct are presented in FIG. 1. A mean of yield values in adjacent rows of unrelated transgenic and non-transgenic hybrid maize (control) is included, with standard deviation indicated. Under the drought conditions, yield was higher in the maize expressing the maize ABI1 dominant mutation under the control of either of the two early kernel promoters.

Example 8

Profiling of Gene Expression in Maize Expressing AtABI1 Mutant

Drought-stressed maize seedlings transgenic for RAB17: AtABI1 (G180D) were analyzed for gene expression relative to expression in control seedlings, using the 8-pack profiling system of Agilent Technologies, Inc. (Santa Clara, Calif.). Presence of the transgene resulted in attenuation of the ABA response. In transgenic plants, expression of drought-induced genes increased under drought stress, but not to the extent seen in control plants. Similarly, in transgenic plants, expression of drought-repressed genes was diminished under drought stress, but not to the extent seen in wild-type plants. Attenuation of the drought response is likewise expected in maize expressing the ZmABI1 mutant.

All publications and patent applications mentioned in the specification are indicative of the level of those skilled in the

TABLE 1

| EST | Gene Name | Sequence | ABA induction | Expression | PPM | SEQ ID NO: |
|---|---|---|---|---|---|---|
| ctst1s.pk017.e5-ctst1s.pk008.c19 | ZM-ABI1 | Full Length | Root & Leaf | kernel, ear, pedicel, seed, meristem, stalk, embryo, husk, leaf, leaf, endosperm, root | 167-900 | 3 and 4 |
| cgs1c.pk001.p19a:fis | ZmABI1_GaspeFlint (ZmABI1-GF) | Full Length | BMS cells | leaf, tassel, kernel, root, embryo, pericarp | 31-72 | 8 |
| p0125.czaaa66r:fis | Homologue A of ZmABI1 | Partial (5') | | | | 5 |
| my.cest1s.pk004.a3 | Homologue B of ZmABI1 | Partial (5') | | | | 6 |
| Ctst1s.pk007.j14a.f:fis | Homologue C of ZmABI1 | Partial (3') | | | | 7 |
| Cie2s.pk005.o3:fis | Homologue of ZmABI1-GF | | | | | 9 |
| | ZMABI1-GF | Amino acid | | | | 10 |
| | ZmABI1-MUT | Nucleic acid | | | | 11 |
| p0005.cbmfd76r.GSS | | genomic | BMS cells | kernel, leaf, root, internode, husk, stalk, silk, pedicel, embryo | 200-2536 | 13 |

art to which this invention pertains. All publications and patent applications are herein incorporated by reference to the same extent as if each individual publication or patent application was specifically and individually indicated to be incorporated by reference.

Although the foregoing invention has been described in some detail by way of illustration for purposes of clarity of understanding, it will be obvious that certain changes and modifications may be practiced within the scope of the appended claims.

That which is claimed:

1. A method for modulating a plant response to abscisic acid (ABA), said method comprising:

introducing into said plant a DNA construct comprising a ZmABI1 nucleic acid encoding a polypeptide having at least 95% identity to SEQ ID NO: 12, operably linked to a heterologous promoter which drives expression in developing seed tissues, wherein the plant response to ABA is modulated.

2. The method of claim 1, wherein said modulating comprises a decreased response to ABA.

3. The method of claim 1, wherein said introducing is by breeding.

4. The method of claim 1, wherein said introducing is by transformation.

5. A method for reducing the detrimental effects of stress on a developing plant seed, said method comprising:

introducing into a plant a DNA construct comprising a ZmABI1 nucleic acid encoding a polypeptide having at least 95% identity to SEQ ID NO: 12, operably linked to a heterologous early kernel/embryo promoter; and expressing said ABA-associated sequence, whereby the detrimental effects of stress are reduced.

6. The method of claim 5, wherein said method comprises a decreased response to ABA.

7. A plant cell having stably introduced a DNA construct comprising a ZmABI1 nucleic acid encoding a polypeptide having at least 95% identity to SEQ ID NO: 12, operably linked to a heterologous early kernel/embryo promoter.

8. The plant cell of claim 7, wherein expression of said ZmABI1 nucleic acid results in a decreased response to ABA.

9. The plant cell of claim 7, wherein said DNA construct is stably integrated into the genome of the plant.

* * * * *

SEQUENCE LISTING

```
<160> NUMBER OF SEQ ID NOS: 13

<210> SEQ ID NO 1
<211> LENGTH: 1981
<212> TYPE: DNA
<213> ORGANISM: Arabidopsis thaliana

<400> SEQUENCE: 1

catttcctcc ttctttctct cttctatctg tgaacaaggc acattagaac tcttcttttc     60

aactttttta ggtgtatata gatgaatcta gaaatagttt tatagttgga aattaattga    120

agagagagag atattactac accaatcttt tcaagaggtc ctaacgaatt acccacaatc    180

caggaaaccc ttattgaaat tcaattcatt tctttctttc tgtgtttgtg attttcccgg    240

gaaatatttt tgggtatatg tctctctgtt tttgctttcc tttttcatag gagtcatgtg    300

tttcttcttg tcttcctagc ttcttctaat aaagtccttc tcttgtgaaa atctctcgaa    360

ttttcatttt tgttccattg gagctatctt atagatcaca accagagaaa aagatcaaat    420

ctttaccgtt aatggaggaa gtatctccgg cgatcgcagg tcctttcagg ccattctccg    480

aaacccagat ggatttcacc gggatcagat tgggtaaagg ttactgcaat aaccaatact    540

caaatcaaga ttccgagaac ggagatctaa tggtttcgtt accggagact tcatcatgct    600

ctgtttctgg gtcacatggt tctgaatcta ggaaagtttt gatttctcgg atcaattctc    660

ctaatttaaa catgaaggaa tcagcagctg ctgatatagt cgtcgttgat atctccgccg    720

gagatgagat caacggctca gatattacta gcgagaagaa gatgatcagc agaacagaga    780

gtaggagttt gtttgaattc aagagtgtgc ctttgtatgg ttttacttcg atttgtggaa    840

gaagacctga gatggaagat gctgtttcga ctataccaag attccttcaa tcttcctctg    900

gttcgatgtt agatggtcgg tttgatcctc aatccgccgc tcatttcttc ggtgtttacg    960

acggccatgg cggttctcag gtagcgaact attgtagaga gaggatgcat ttggctttgg   1020

cggaggagat agctaaggag aaaccgatgc tctgcgatgg tgatacgtgg ctggagaagt   1080

ggaagaaagc tcttttcaac tcgttcctga gagttgactc ggagattgag tcagttgcgc   1140

cggagacggt tgggtcaacg tcggtggttg ccgttgtttt cccgtctcac atcttcgtcg   1200

ctaactgcgg tgactctaga gccgttcttt gccgcggcaa aactgcactt ccattatccg   1260

ttgaccataa accggataga gaagatgaag ctgcgaggat tgaagccgca ggagggaaag   1320

tgattcagtg gaatggagct cgtgttttcg gtgttctcgc catgtcgaga tccattggcg   1380

atagatactt gaaaccatcc atcattcctg atccggaagt gacggctgtg aagagagtaa   1440

aagaagatga ttgtctgatt ttggcgagtg acggggtttg ggatgtaatg acggatgaag   1500

aagcgtgtga gatggcaagg aagcggattc tcttgtggca caagaaaaac gcggtggctg   1560

gggatgcatc gttgctcgcg gatgagcgga gaaaggaagg gaaagatcct gcggcgatgt   1620

ccgcggctga gtatttgtca aagctggcga tacagagagg aagcaaagac aacataagtg   1680

tggtggtggt tgatttgaag cctcggagga aactcaagag caaacccttg aactgaggca   1740

gagagggtcc tttttcttaa tttttaaaat gaatatgggt ctctccaaga aaaagtattt   1800

actattatta atttgtgctt atttttttaa ctaacaagtt ataaccatat ggagataatg   1860
```

```
aagcttaatg tgttaagctc ttttgtcttg actacattct aaaaagcccc ttgtattttt   1920

cttcccgggc taattgtaat atggttacaa catacattaa gatgtagtat tattgtttaa   1980

a                                                                   1981


<210> SEQ ID NO 2
<211> LENGTH: 434
<212> TYPE: PRT
<213> ORGANISM: Arabidopsis thaliana

<400> SEQUENCE: 2

Met Glu Glu Val Ser Pro Ala Ile Ala Gly Pro Phe Arg Pro Phe Ser
1               5                   10                  15

Glu Thr Gln Met Asp Phe Thr Gly Ile Arg Leu Gly Lys Gly Tyr Cys
            20                  25                  30

Asn Asn Gln Tyr Ser Asn Gln Asp Ser Glu Asn Gly Asp Leu Met Val
        35                  40                  45

Ser Leu Pro Glu Thr Ser Ser Cys Ser Val Ser Gly Ser His Gly Ser
    50                  55                  60

Glu Ser Arg Lys Val Leu Ile Ser Arg Ile Asn Ser Pro Asn Leu Asn
65                  70                  75                  80

Met Lys Glu Ser Ala Ala Ala Asp Ile Val Val Val Asp Ile Ser Ala
                85                  90                  95

Gly Asp Glu Ile Asn Gly Ser Asp Ile Thr Ser Glu Lys Lys Met Ile
            100                 105                 110

Ser Arg Thr Glu Ser Arg Ser Leu Phe Glu Phe Lys Ser Val Pro Leu
        115                 120                 125

Tyr Gly Phe Thr Ser Ile Cys Gly Arg Arg Pro Glu Met Glu Asp Ala
    130                 135                 140

Val Ser Thr Ile Pro Arg Phe Leu Gln Ser Ser Ser Gly Ser Met Leu
145                 150                 155                 160

Asp Gly Arg Phe Asp Pro Gln Ser Ala Ala His Phe Phe Gly Val Tyr
                165                 170                 175

Asp Gly His Gly Gly Ser Gln Val Ala Asn Tyr Cys Arg Glu Arg Met
            180                 185                 190

His Leu Ala Leu Ala Glu Glu Ile Ala Lys Glu Lys Pro Met Leu Cys
        195                 200                 205

Asp Gly Asp Thr Trp Leu Glu Lys Trp Lys Lys Ala Leu Phe Asn Ser
    210                 215                 220

Phe Leu Arg Val Asp Ser Glu Ile Glu Ser Val Ala Pro Glu Thr Val
225                 230                 235                 240

Gly Ser Thr Ser Val Val Ala Val Val Phe Pro Ser His Ile Phe Val
                245                 250                 255

Ala Asn Cys Gly Asp Ser Arg Ala Val Leu Cys Arg Gly Lys Thr Ala
            260                 265                 270

Leu Pro Leu Ser Val Asp His Lys Pro Asp Arg Glu Asp Glu Ala Ala
        275                 280                 285

Arg Ile Glu Ala Ala Gly Gly Lys Val Ile Gln Trp Asn Gly Ala Arg
    290                 295                 300

Val Phe Gly Val Leu Ala Met Ser Arg Ser Ile Gly Asp Arg Tyr Leu
305                 310                 315                 320

Lys Pro Ser Ile Ile Pro Asp Pro Glu Val Thr Ala Val Lys Arg Val
                325                 330                 335

Lys Glu Asp Asp Cys Leu Ile Leu Ala Ser Asp Gly Val Trp Asp Val
            340                 345                 350
```

-continued

```
Met Thr Asp Glu Glu Ala Cys Glu Met Ala Arg Lys Arg Ile Leu Leu
        355                 360                 365

Trp His Lys Lys Asn Ala Val Ala Gly Asp Ala Ser Leu Leu Ala Asp
    370                 375                 380

Glu Arg Arg Lys Glu Gly Lys Asp Pro Ala Ala Met Ser Ala Ala Glu
385                 390                 395                 400

Tyr Leu Ser Lys Leu Ala Ile Gln Arg Gly Ser Lys Asp Asn Ile Ser
                405                 410                 415

Val Val Val Val Asp Leu Lys Pro Arg Arg Lys Leu Lys Ser Lys Pro
            420                 425                 430

Leu Asn


<210> SEQ ID NO 3
<211> LENGTH: 2130
<212> TYPE: DNA
<213> ORGANISM: Zea mays
<220> FEATURE:
<221> NAME/KEY: CDS
<222> LOCATION: (432)...(1886)

<400> SEQUENCE: 3

ccgagccaca gcaattaccc agctcagcgg ctgccgaacc ccctccgctt cccggctctc      60

caggtcgaga agggcgctgc tcgccacctg cctttctttc tacagttcga cgcactttgg     120

tggcggtgcc gctactctcc ttcccgagtt cctaacttcc taactaggag ggcgggcgtt     180

gtctgcctgt gtgcttttgg cgattcgggg gcttgggctc ggatctgcgc gtgccttcct     240

ccggacccga gcgaggctcg ggcgcgaatt tggggcggat cagcgcagat ctggaggcac     300

atgaggagga ggaggcggag gggtagcggg agcgatgcgg tgcttctgcg aagggcttga     360

gccgacctgg gaaggtgatt ctggaggagg tggcggtggc tgcggaggcg gaggggggagg    420

ctggaggagg g atg gaa gac gtc gta gca gtc gtg gcg tca ctc tcc gcg      470
             Met Glu Asp Val Val Ala Val Val Ala Ser Leu Ser Ala
             1               5                   10

ccg ccg gcg ccg gcg ttt agc ccc gcc gcg gcg ggg ctc acg ctg atc       518
Pro Pro Ala Pro Ala Phe Ser Pro Ala Ala Ala Gly Leu Thr Leu Ile
    15                  20                  25

gcc gcg gcg gtc gcg gac ccg atc gcc gcg gtg gtc gtc gga gcc atg       566
Ala Ala Ala Val Ala Asp Pro Ile Ala Ala Val Val Val Gly Ala Met
30                  35                  40                  45

gag ggg gtc tcc gtg ccc gtg act gtg ccc ccg gtc agg acg gcg tcc       614
Glu Gly Val Ser Val Pro Val Thr Val Pro Pro Val Arg Thr Ala Ser
                50                  55                  60

gcg gtg gac gac gac gcg ctg gcg ccg gga gag gaa ggg gga gac gcc       662
Ala Val Asp Asp Asp Ala Leu Ala Pro Gly Glu Glu Gly Gly Asp Ala
            65                  70                  75

tct ttg gcc ggg agc ccg tgc tcg gtg gtc agc gac tgt agc agc gtg       710
Ser Leu Ala Gly Ser Pro Cys Ser Val Val Ser Asp Cys Ser Ser Val
        80                  85                  90

gcc agc gct gat ttc gag ggg gtc ggg ctg tgt ttc ttc ggc gcg gca       758
Ala Ser Ala Asp Phe Glu Gly Val Gly Leu Cys Phe Phe Gly Ala Ala
    95                  100                 105

gca ggc gcg gag ggt ggt ccc atg gtg ttg gag gac tcg acc gcg tct       806
Ala Gly Ala Glu Gly Gly Pro Met Val Leu Glu Asp Ser Thr Ala Ser
110                 115                 120                 125

gca gcc acg gtc gag gcg gag gcc agg gtc gcg gct ggt ggg agg agt       854
Ala Ala Thr Val Glu Ala Glu Ala Arg Val Ala Ala Gly Gly Arg Ser
                130                 135                 140

gtc ttc gcc gtg gac tgc gtg ccg ctg tgg ggc tac act tcc ata tgc       902
```

```
Val Phe Ala Val Asp Cys Val Pro Leu Trp Gly Tyr Thr Ser Ile Cys
            145                 150                 155

ggc cgc cgt ccg gag atg gag gat gcc gtt gct ata gtg ccg cga ttc      950
Gly Arg Arg Pro Glu Met Glu Asp Ala Val Ala Ile Val Pro Arg Phe
        160                 165                 170

ttt gac ttg cca ctc tgg ttg ctc acc ggc aat gcg atg gtc gat ggc      998
Phe Asp Leu Pro Leu Trp Leu Leu Thr Gly Asn Ala Met Val Asp Gly
    175                 180                 185

ctc gat ccc atg acg ttc cgc tta cct gca cat ttc ttt ggt gtc tat     1046
Leu Asp Pro Met Thr Phe Arg Leu Pro Ala His Phe Phe Gly Val Tyr
190                 195                 200                 205

gac gga cac ggt ggt gca cag gta gca aat tac tgt cgg gaa cgc ctc     1094
Asp Gly His Gly Gly Ala Gln Val Ala Asn Tyr Cys Arg Glu Arg Leu
            210                 215                 220

cat gtg gcc cta ctg gag cag ctg agc agg ata gag gag act gcg tgt     1142
His Val Ala Leu Leu Glu Gln Leu Ser Arg Ile Glu Glu Thr Ala Cys
            225                 230                 235

gca gct aac ttg gga gac atg gag ttc aag aaa cag tgg gaa aag gtc     1190
Ala Ala Asn Leu Gly Asp Met Glu Phe Lys Lys Gln Trp Glu Lys Val
        240                 245                 250

ttt gtg gat tct tat gct aga gtg gat gac gag gtt ggg gga aac acg     1238
Phe Val Asp Ser Tyr Ala Arg Val Asp Asp Glu Val Gly Gly Asn Thr
    255                 260                 265

atg agg gga ggt ggt gaa gaa gca ggc aca agt gat gct gct atg aca     1286
Met Arg Gly Gly Gly Glu Glu Ala Gly Thr Ser Asp Ala Ala Met Thr
270                 275                 280                 285

ctc gtg cca gaa cct gtg gca cct gag acg gtg ggt tcg acg gcg gtc     1334
Leu Val Pro Glu Pro Val Ala Pro Glu Thr Val Gly Ser Thr Ala Val
                290                 295                 300

gtc gct gtc atc tgc tcc tca cat atc att gtc tcc aac tgt gga gat     1382
Val Ala Val Ile Cys Ser Ser His Ile Ile Val Ser Asn Cys Gly Asp
            305                 310                 315

tca cgg gca gtg ctc tgc cga ggc aag cag cct gtg cct ctg tcg gtg     1430
Ser Arg Ala Val Leu Cys Arg Gly Lys Gln Pro Val Pro Leu Ser Val
        320                 325                 330

gat cat aaa cct aac agg gag gat gag tat gca agg att gag gca gag     1478
Asp His Lys Pro Asn Arg Glu Asp Glu Tyr Ala Arg Ile Glu Ala Glu
    335                 340                 345

ggt ggc aag gtc ata caa tgg aac ggt tat cga gtt ttc ggt gtt ctt     1526
Gly Gly Lys Val Ile Gln Trp Asn Gly Tyr Arg Val Phe Gly Val Leu
350                 355                 360                 365

gca atg tcg cga tca att ggt gac aga tat ctg aag cca tgg ata att     1574
Ala Met Ser Arg Ser Ile Gly Asp Arg Tyr Leu Lys Pro Trp Ile Ile
                370                 375                 380

cca gtc cca gag gta aca ata gtt ccg cgg gct aag gat gac gag tgc     1622
Pro Val Pro Glu Val Thr Ile Val Pro Arg Ala Lys Asp Asp Glu Cys
            385                 390                 395

ctt att ctt gcc agt gac ggc ctc tgg gat gta atg tca aat gaa gag     1670
Leu Ile Leu Ala Ser Asp Gly Leu Trp Asp Val Met Ser Asn Glu Glu
        400                 405                 410

gta tgt gaa atc gct cgc aag cgg ata ctt ctg tgg cac aaa aag aac     1718
Val Cys Glu Ile Ala Arg Lys Arg Ile Leu Leu Trp His Lys Lys Asn
    415                 420                 425

agc aca agc tca tca tca gcc cca cgg gtt ggt gac tcc gca gac tca     1766
Ser Thr Ser Ser Ser Ser Ala Pro Arg Val Gly Asp Ser Ala Asp Ser
430                 435                 440                 445

gcc gct caa gcg gct gct gaa tgc ttg tca aag ctt gct ctt cag aag     1814
Ala Ala Gln Ala Ala Ala Glu Cys Leu Ser Lys Leu Ala Leu Gln Lys
                450                 455                 460

ggg agc aaa gac aac att act gtc gtg gta gtt gat ctg aaa gca cag     1862
```

```
Gly Ser Lys Asp Asn Ile Thr Val Val Val Val Asp Leu Lys Ala Gln
            465                 470                 475

cgc aag ttc aag agc aaa act taa ccgtgacaag cgtagcaaca agttgctaag    1916
Arg Lys Phe Lys Ser Lys Thr  *
        480

aacctataga ttcggacagt cccaagttcg gtcattttag ttcgctgctt tagtgcattg   1976

cttagcccag ttccttattt ttctcagttc tttttaagcc atgccaaggg ctgtattccc   2036

cgtatacggt acagatcgcg aaatccctat cagggatggt ttggtgatat cagggtttat   2096

atgttttcct gaccgtggtg actgtcctgt tttc                               2130


<210> SEQ ID NO 4
<211> LENGTH: 484
<212> TYPE: PRT
<213> ORGANISM: Zea mays

<400> SEQUENCE: 4

Met Glu Asp Val Val Ala Val Val Ala Ser Leu Ser Ala Pro Pro Ala
1               5                   10                  15

Pro Ala Phe Ser Pro Ala Ala Ala Gly Leu Thr Leu Ile Ala Ala Ala
            20                  25                  30

Val Ala Asp Pro Ile Ala Ala Val Val Val Gly Ala Met Glu Gly Val
        35                  40                  45

Ser Val Pro Val Thr Val Pro Pro Val Arg Thr Ala Ser Ala Val Asp
    50                  55                  60

Asp Asp Ala Leu Ala Pro Gly Glu Glu Gly Gly Asp Ala Ser Leu Ala
65                  70                  75                  80

Gly Ser Pro Cys Ser Val Val Ser Asp Cys Ser Ser Val Ala Ser Ala
                85                  90                  95

Asp Phe Glu Gly Val Gly Leu Cys Phe Phe Gly Ala Ala Ala Gly Ala
            100                 105                 110

Glu Gly Gly Pro Met Val Leu Glu Asp Ser Thr Ala Ser Ala Ala Thr
        115                 120                 125

Val Glu Ala Glu Ala Arg Val Ala Ala Gly Gly Arg Ser Val Phe Ala
    130                 135                 140

Val Asp Cys Val Pro Leu Trp Gly Tyr Thr Ser Ile Cys Gly Arg Arg
145                 150                 155                 160

Pro Glu Met Glu Asp Ala Val Ala Ile Val Pro Arg Phe Phe Asp Leu
                165                 170                 175

Pro Leu Trp Leu Leu Thr Gly Asn Ala Met Val Asp Gly Leu Asp Pro
            180                 185                 190

Met Thr Phe Arg Leu Pro Ala His Phe Phe Gly Val Tyr Asp Gly His
        195                 200                 205

Gly Gly Ala Gln Val Ala Asn Tyr Cys Arg Glu Arg Leu His Val Ala
    210                 215                 220

Leu Leu Glu Gln Leu Ser Arg Ile Glu Glu Thr Ala Cys Ala Ala Asn
225                 230                 235                 240

Leu Gly Asp Met Glu Phe Lys Lys Gln Trp Glu Lys Val Phe Val Asp
                245                 250                 255

Ser Tyr Ala Arg Val Asp Asp Glu Val Gly Gly Asn Thr Met Arg Gly
            260                 265                 270

Gly Gly Glu Glu Ala Gly Thr Ser Asp Ala Ala Met Thr Leu Val Pro
        275                 280                 285

Glu Pro Val Ala Pro Glu Thr Val Gly Ser Thr Ala Val Val Ala Val
    290                 295                 300
```

```
Ile Cys Ser Ser His Ile Ile Val Ser Asn Cys Gly Asp Ser Arg Ala
305                 310                 315                 320

Val Leu Cys Arg Gly Lys Gln Pro Val Pro Leu Ser Val Asp His Lys
                325                 330                 335

Pro Asn Arg Glu Asp Glu Tyr Ala Arg Ile Glu Ala Glu Gly Gly Lys
            340                 345                 350

Val Ile Gln Trp Asn Gly Tyr Arg Val Phe Gly Val Leu Ala Met Ser
        355                 360                 365

Arg Ser Ile Gly Asp Arg Tyr Leu Lys Pro Trp Ile Ile Pro Val Pro
    370                 375                 380

Glu Val Thr Ile Val Pro Arg Ala Lys Asp Asp Glu Cys Leu Ile Leu
385                 390                 395                 400

Ala Ser Asp Gly Leu Trp Asp Val Met Ser Asn Glu Glu Val Cys Glu
                405                 410                 415

Ile Ala Arg Lys Arg Ile Leu Leu Trp His Lys Lys Asn Ser Thr Ser
            420                 425                 430

Ser Ser Ser Ala Pro Arg Val Gly Asp Ser Ala Asp Ser Ala Ala Gln
        435                 440                 445

Ala Ala Ala Glu Cys Leu Ser Lys Leu Ala Leu Gln Lys Gly Ser Lys
    450                 455                 460

Asp Asn Ile Thr Val Val Val Val Asp Leu Lys Ala Gln Arg Lys Phe
465                 470                 475                 480

Lys Ser Lys Thr


<210> SEQ ID NO 5
<211> LENGTH: 941
<212> TYPE: DNA
<213> ORGANISM: Zea mays

<400> SEQUENCE: 5

cggacgcgtg ggcggacgcg tgggccggcc actcccggct cccgagccac agcaattacc      60

cagctcagcg gctgccgaac cccctccgct tcccggctct ccaggtcgag aagggcgctg     120

ctcgccacct gccttccttt ctacagttcg acgcactttg gtggtggtgc cgctactctc     180

ctcccgagtt ccttccttcc taactaggag ggcgggcgtt gcctgcctgt gtgcttttgg     240

cgattcgggg gcttgggctc ggatctgcgc gtgcctgcct ccggacccga gcgaggctcg     300

ggcgcgaatt tggggcggat cagcgcagat ctggaggcac atgaggagga ggaggcggaa     360

ggggtagcgg gagcgatgcg gtgcttctgc gaagggcttg agccgacctg ggaaggtgat     420

tctggaggag gtggcggtgg ctgcggaggc ggaggggggag gctggaggag ggatggaaga     480

catcgtagca gtcgtggcgt cactctccgc gccgccggcg ccggcgttta gccccgccgc     540

ggcggggctc acgctgatcg ccgcggcggt cgcggacccg atcgccgcgg tggtcgtcgg     600

agccatggag ggggtctccg tgcccgtgac tgtgccccccg gtcaggacgg cgtccgcggt     660

ggacgacgac gcgctggcgc cgggagagga agggggagac gcctctttgg ccgggagccc     720

gtgctcggtg gtcagcgact gcagcagcgt ggccagcgct gatttcgagg gggtcgggct     780

gtgtttcttc agcgcggcag caggcgcgga gggtggtccc atggtgttgg aggactcgac     840

cgcgtctgcg gccacggtcg aggcggaggc cagggtcgcg gctggtggga ggagtgtctt     900

cgccgtggac tgcgtgccgc tgtggggcta cacttccata t                         941


<210> SEQ ID NO 6
<211> LENGTH: 878
<212> TYPE: DNA
<213> ORGANISM: Zea mays
```

<400> SEQUENCE: 6

```
aattacccag tcccagatca acgttaccca acggctgcca aatctccctc cgcttcccgg     60
ctccccaggt cgagccgtcg agggcgctgc ttgccactgc cttggtcgct actgtacgac    120
gcactttggt ggtggtgccg ctactctgct ccccgagttc catccttcct cacgaggagg    180
gcgggcgttg ccgttgcctg cccgtgtgct ttggcgattc gggggcttgg gctcggatct    240
gcgtgtgcct gcctccggac ccgcccgagg ctcggggcgc ctgatttggg gccgggttag    300
gcagatctgg agggcacatg agaataaggc ggcggcggag gggtagcggg agctatgcgg    360
tgcttctgcg aaggacttga gccggcctgg gaaggtgatc ctggaggagg ttgcggcggc    420
tgcaacggcg gagggaaggc tggaggatgt cgtagcggtc gtggcgccgc tcgcggctcc    480
gcctgcgccg acgtttagcc ccgctgcggc ggagctcacg ctgatcgccg cggcggtcgt    540
gggagccatg gagggggtct ccgtgccccc ggtcaggacg gcctccgcgg cggacgacga    600
cgcgctggcg ccggaagggg aagggggaga cgcgtctctg gccgggagcc cgtgctcggt    660
ggccagcgac tgcagcagcg tggccagcgc tgacttcgag gggtcggga tgggtttctt    720
cggcgcggca gcgggcgcgg agggtggcct tggccccatg gtgttcgagg actcggccgc    780
gtccgcggcc acggtcgagg cggaggccag ggtcgcagct ggtgggagga gtgtcttcgc    840
cgtggactgc gtgccgctgt ggggctacac cactatat                           878
```

<210> SEQ ID NO 7
<211> LENGTH: 1299
<212> TYPE: DNA
<213> ORGANISM: Zea mays

<400> SEQUENCE: 7

```
gccggagatg gaggatgccg ttgctatagt gccgcgattc tttgacgtgc cactctggat     60
gctcaccggc aatgcggtgg tcgatgggct cgatcccatg acgttccgat tacctgcaca    120
tttctttggt gtctatgacg gacatggtgg tgcacaggta gcaaattact gtcgggaacg    180
cctccatggg gccctactgg agcagctgag caggatagag cagaccgtgt gcgcagctaa    240
cttgggagac atggaattca agaaacagtg ggaaaaggcc tttgtggatt ctttcgctag    300
agtggatgac gatgttgggg gcaagacgat cagggaagat ggtggcgaag cacgcataag    360
tgacgctgct atgatgcttg tgcccgaacc tgtggcacct gagaccgtgg gttcaacggc    420
ggtcgtcgcc gtcatctgct cctcgcatat cattgtctcc aattgtggag attcacgggc    480
ggtgctctgc cgtggcaagc agcccgtgcc tctgtcggtg gatcataaac ctaacaggga    540
agatgagtat gcaaggattg aggcagaggg tggtaaggtc atacaatgga atggttatcg    600
agtttttggt gttcttgcaa tgtcgcgatc aattggtgac agatatctga agccatggat    660
aattccagtc ccggaggtaa caatagttcc gcgggctaag gatgatgagt gccttattct    720
tgctagcgac ggcctttggg acgtaatctc aaatgaagag gtatgtgaag ttgctcgcaa    780
gcggatactt ctgtggcaca aaaagaatgg cacaagctca tcatcagccc cacgggttgg    840
tgattccgca gacgcagctg ctcaagcggc tgccgaatgc ttgtcaaagc ttgctcttca    900
gaaggggagc aaagacaaca tcactgtcgt tgtagttgac ctgaaagcac agcgtaagtt    960
caagagcaaa acctaaccat gatgacttaa tggacaatta tagcgacaag ttgctaggaa   1020
cctatagatt tggagaatcc aaatttggtc agtttagtcg ctgccttagt acattactta   1080
gcctagttct ttttaagcaa tttgggctgc caaaggtttg tattcctgta tatggtacaa   1140
attgtaaaat ccgtgccagg gtttatgttt cctgaccgtg gcgacggtcc tgttttcact   1200
```

```
cttctttctt cattgccctg tattcttttt gtctgcattc ttttttgtca agcttggcgt   1260

ccaagtatct gtcaatgtat tttttttacc aaaaaaaaa                          1299
```

<210> SEQ ID NO 8
<211> LENGTH: 3023
<212> TYPE: DNA
<213> ORGANISM: Zea mays

<400> SEQUENCE: 8

```
tggagttgag ggagctcctg aacggctacg ccaacgcggt ggccacccgc gcggccaccg     60

gtgccgctgg ggcgacagca gagaagttga aagagctgat ggggaactcc gagcccgagg    120

cgctgatggc gggcttccaa cccgaagacg tgctgccgga cgcaccggcg aggttcgtga    180

gatgggtgac gggcctcaat aagaagctcg aagacttggt ggagtcgtgg gacaagttcc    240

tgtccgatat agtggccgca cacaaggaga aggggggtgg cgacgcagag gaggatgagg    300

acttcttgga tgtcttgctt cggctgcggg aagaaggcgc agatgggctc gagctcacag    360

acgatcgcat caaagctacc gtcaaggaca tgatagcggc tgcaactgaa acatcgtccc    420

aaacgctgga atggaccatg gccgaactca ttgccaaccc gcgggtgatg agcaagctcc    480

aaggcgagat agcgcgagtc gtcagcgccg ctcctcgtcc cgcacgaatc aacaacgccc    540

gcggttgtgc agggctacga gatcccggcc aagacggctc tcttcgtcaa cgtgtgggcc    600

atcgggcggg accctgctgt gtgggacgca ccggacgagt tccgcccaga gcggttcgtg    660

ggcggcagtc cctcggtgga cttcagaggt accgactacc agctcatccc gttcggcgcc    720

ggccggagga tctgccccgg catcaacttc gcgctgccgg tcttggagct cgcgcttgtc    780

agccttctgc accacttcga atgggagctc cccgccggcg tgggaaaggc ggacctcgac    840

gtgggcgagg cgccggggat gacgacgccg cggcggattc cgctcgtcct tgtccccaag    900

tgcaggacgc tcgttcagcc agcactgcag tagcgcgagg aatttcatgt gtctccatgc    960

agtggcggaa ccagaaatat ttaagagctt gggtaaaaaa taatacttat actgtaaata   1020

tgtagctttg tctaattttt accagtgttt aactatattt tactacttgt tgtatgtgta   1080

taagttcact agcaataatg gaggagccta tcctcttgcc cccaaaaaaa aaaaaaaggg   1140

cggccgccct tttttttttt tttttttttt tttttttttt tttttttttt tttttagcac   1200

agatacagtg ctcaattagg tagttcaggg gtggcagttt ctattgtacc tttacctgtt   1260

aataacagaa acaatgcccc aaacccaatc agtgaactac ttgttggaat ctacatatgt   1320

atgttatttc taagatttgg accctagaat cgaccacctt acctagccag cccagtctcc   1380

aaccagatta catctgtgta tgaatctgta ccctgatcaa acgtggcagc ctatatggtt   1440

gtgggaaaga aaaagaaaaa aaggctaaac aggagcattt tctcaacctt tctagcgtct   1500

attgttactg tccaagtctt accgaatccg tggttatgtt ctgctcttga actttctatg   1560

tgacttgagg tcgactacaa tgacggtaat gttgtccttg ctccccttct ggagggccag   1620

cttcgacaaa tattcagcag ctgcttgagc tgcttcatct gccgaatcac cgcttctttg   1680

ggctgacgct gagacgtcgc cgttcttctt gtgccacagc agtatgcgct tgcgagcagc   1740

atcacatacc tcctcgtttg acattacatc ccacaggcca tcgcttgcaa gaattaggca   1800

ctcatcatcc tttgcacggg cgacaattgt gacctcaggg actgggatta tatatggctt   1860

caggtacctg tccccaattg accgggacat ggcaagaaca ccgagaactc ggtatccgtt   1920

ccagttgatg accttgcccc cctgggcctc gatcctcgca tactcatctt ccctgtttgg   1980

tttatggtcc acggacagcg gcaggggctg cttgccccgg cagagcaccg ccctcgagtc   2040
```

gccgcagttg gcaacgatga catgcgatga gcagacgagc gcaaccaccg ctgttgaccc 2100
cactgtgtct ggagccacag gcttggttcc ggtcgccgcg tctcctccca cctctgcatc 2160
aacacggctg aagcagtcca caaagacctt ctcccagtgc tcgtgagtac tagggtcaag 2220
gccactcaag tcagcgtcgg acacggcctg ctctgccctg gtgagcccct cggccagtac 2280
ctcgtgcatt ctgtcccggc agtagttggc gacctgaagg ccgccgtggc cgtcgtagac 2340
ggcgaagaag tgcgcgggga ggcggaagga tgcccggtcg aggccgtcga cgggcgcgtc 2400
gccggcgagc atccagagcg ggacgtggaa gaaggttggg agcacgcggg cggcgtcctc 2460
catctcgggc cgtcggccgc acacggagtg gagtccccag cgcggcacgc agtcgagcgc 2520
gaagacgctc ctggcggccc tgggcccgga ggcggggagc gagctggcgg aggcggaggc 2580
ggaggcgggg gagacgaggt cgtcgagcac gagcgtggag gcgaggtcgg cgaagccctc 2640
gaagtcggcg gtggcgacgc tgctgcagtc ggagcaggga ctcccgggcg cggactcggg 2700
ctccggcggt ggcatcccgg ccccggcggc agcaggagcg gagtcgtcta tgaagtcagc 2760
gacggcggcg aagagtgcga gggcccccgg ggcgaggtcc tccatgggct cggtcacggc 2820
agggagccat tggcagtagt ggcctcgcgt cggggggtca tgggcatggc cgcatgggca 2880
tgggggtgcg tggcgggggc tcgcaggcag atctgaaaag ggtgggagag ggacgggacg 2940
ggctggatgg gatcgaatcc aggagtaggt gaggggagat cagggtgtca cgggcggtgc 3000
cctggctgca acggaagccg cct 3023

<210> SEQ ID NO 9
<211> LENGTH: 1684
<212> TYPE: DNA
<213> ORGANISM: Zea mays

<400> SEQUENCE: 9
cggacgcgtg ggcgcgaggc cactactgcc aatggctccc tgccgtgacc gagcccatgg 60
aggacctcgc cccgggggcc ctcgcgctct tcgccgccgt cgctgacttc atagacgact 120
ccgctcccgc tgccgccggg gccgggatgc caccgccgga gcccgagtcc gcgcccggga 180
gtccctgctc cgactgcagc agcgtcgcca ccgccgactt cgagggcttc gccgacctcg 240
cctccacgct cgtgctcgac gacctcgtct cccccgcctc cgcctccgcc tccgccagct 300
cgctccccgc ctccgggccc agggccgcca ggagcgtctt cgcgctcgac tgcgtgccgc 360
gctggggact ccactccgtg tgcggccgac ggcccgagat ggaggacgcc gcccgcgtgc 420
tcccaacctt cttccacgtc ccgctctgga tgctcgccgg cgacgcgccc gtcgacggcc 480
tcgaccgggc atccttccgc ctccccgcgc acttcttcgc cgtctacgac ggccacggcg 540
gccttcaggt cgccaactac tgccgggaca gaatgcacga ggtactggcc gaggggctca 600
ccagggcaga gcaggccgtg tccgacgctg acttgagtgg ccttgaccct agtactcacg 660
agcactggga gaaggtcttt gtggactgct tcagccgtgt tgatgcagag gtgggaggag 720
acgcggcgac cggaaccaag cctgtggctc cagacacagt ggggtcaaca gcggtggttg 780
cgctcgtctg ctcatcgcat gtcatcgttg ccaactgcgg cgactcgagg gcggtgctct 840
gccggggcaa gcagcccctg ccgctgtccg tggaccataa accaaacagg gaagatgagt 900
atgcgaggat cgaggcccag gggggcaagg tcatcaactg gaacggctac cgagttctcg 960
gtgttcttgc catgtcccgg tcaattgggg acaggtacct gaagccatat ataatcccag 1020
tccctgaggt cacaattgtc gcccgtgcaa aggatgatga gtgcctaatt cttgcaagcg 1080
atggcctgtg ggatgtaatg tcaaacgagg aggtatgtga tgctgctcgc aagcgcatac 1140

```
tgctgtggca caagaagaac ggcgacgact cagcgtcagc ccaaagaagc ggtgattcgg   1200

cagatgaagc agctcaagca gctgctgaat atttgtcgaa gctggccctc cagaagggga   1260

gcaaggacaa cattaccgtc attgtagtcg acctcaagtc acatagaaag ttcaagagca   1320

gaacataacc acggattcgg taagacttgg acagtaacaa tagacgctag gaaggttgag   1380

aaaatgctcc tgtttaccct tttttttct ttttctttcc cacaaccata taggctgcca   1440

cgtttgatca gggtacagat tcatacacag atgtaatctg gttggagact gggctggcta   1500

ggtaaggtgg tcgattctag ggtccaaatc ttagaaataa catacatatg tagattccaa   1560

caagtagttc actgattggg tttggggcat tgtttctgtt attaacaggt aaaggtacaa   1620

tagaaactgc cacccctgaa ctaaaaaaaa aaaaaaaaaa aaaaaaaaaa aaaaaaaaaa   1680

aaaa                                                                1684
```

```
<210> SEQ ID NO 10
<211> LENGTH: 423
<212> TYPE: PRT
<213> ORGANISM: Zea mays

<400> SEQUENCE: 10

Met Glu Asp Leu Ala Pro Gly Ala Leu Ala Leu Phe Ala Ala Val Ala
1               5                   10                  15

Asp Phe Ile Asp Asp Ser Ala Pro Ala Ala Ala Gly Ala Gly Met Pro
            20                  25                  30

Pro Pro Glu Pro Glu Ser Ala Pro Gly Ser Pro Cys Ser Asp Cys Ser
        35                  40                  45

Ser Val Ala Thr Ala Asp Phe Glu Gly Phe Ala Asp Leu Ala Ser Thr
    50                  55                  60

Leu Val Leu Asp Asp Leu Val Ser Pro Ala Ser Ala Ser Ala Ser Ala
65                  70                  75                  80

Ser Ser Leu Pro Ala Ser Gly Pro Arg Ala Ala Arg Ser Val Phe Ala
                85                  90                  95

Leu Asp Cys Val Pro Arg Trp Gly Leu His Ser Val Cys Gly Arg Arg
            100                 105                 110

Pro Glu Met Glu Asp Ala Ala Arg Val Leu Pro Thr Phe Phe His Val
        115                 120                 125

Pro Leu Trp Met Leu Ala Gly Asp Ala Pro Val Asp Gly Leu Asp Arg
    130                 135                 140

Ala Ser Phe Arg Leu Pro Ala His Phe Phe Ala Val Tyr Asp Gly His
145                 150                 155                 160

Gly Gly Leu Gln Val Ala Asn Tyr Cys Arg Asp Arg Met His Glu Val
                165                 170                 175

Leu Ala Glu Gly Leu Thr Arg Ala Glu Gln Ala Val Ser Asp Ala Asp
            180                 185                 190

Leu Ser Gly Leu Asp Pro Ser Thr His Glu His Trp Glu Lys Val Phe
        195                 200                 205

Val Asp Cys Phe Ser Arg Val Asp Ala Glu Val Gly Gly Asp Ala Ala
    210                 215                 220

Thr Gly Thr Lys Pro Val Ala Pro Asp Thr Val Gly Ser Thr Ala Val
225                 230                 235                 240

Val Ala Leu Val Cys Ser Ser His Val Ile Val Ala Asn Cys Gly Asp
                245                 250                 255

Ser Arg Ala Val Leu Cys Arg Gly Lys Gln Pro Leu Pro Leu Ser Val
            260                 265                 270
```

```
Asp His Lys Pro Asn Arg Glu Asp Glu Tyr Ala Arg Ile Glu Ala Gln
        275                 280                 285

Gly Gly Lys Val Ile Asn Trp Asn Gly Tyr Arg Val Leu Gly Val Leu
    290                 295                 300

Ala Met Ser Arg Ser Ile Gly Asp Arg Tyr Leu Lys Pro Tyr Ile Ile
305                 310                 315                 320

Pro Val Pro Glu Val Thr Ile Val Ala Arg Ala Lys Asp Asp Glu Cys
                325                 330                 335

Leu Ile Leu Ala Ser Asp Gly Leu Trp Asp Val Met Ser Asn Glu Glu
            340                 345                 350

Val Cys Asp Ala Ala Arg Lys Arg Ile Leu Leu Trp His Lys Lys Asn
        355                 360                 365

Gly Asp Val Ser Ala Ser Ala Gln Arg Ser Gly Asp Ser Ala Asp Glu
    370                 375                 380

Ala Ala Gln Ala Ala Ala Glu Tyr Leu Ser Lys Leu Ala Leu Gln Lys
385                 390                 395                 400

Gly Ser Lys Asp Asn Ile Thr Val Ile Val Val Asp Leu Lys Ser His
                405                 410                 415

Arg Lys Phe Lys Ser Arg Thr
            420


<210> SEQ ID NO 11
<211> LENGTH: 1407
<212> TYPE: DNA
<213> ORGANISM: Zea mays
<220> FEATURE:
<221> NAME/KEY: CDS
<222> LOCATION: (1)...(1407)
<220> FEATURE:
<221> NAME/KEY: mutation
<222> LOCATION: (577)...(579)
<223> OTHER INFORMATION: G to D mutation at aa 193 corresponds to aa
      209 of wt

<400> SEQUENCE: 11

atg gaa gac gtc gta gca gtc gtg gcg tca ctc tcc gcg ccg ccg gcg       48
Met Glu Asp Val Val Ala Val Val Ala Ser Leu Ser Ala Pro Pro Ala
1               5                   10                  15

ccg gcg ttt agc ccc gcc gcg gtg gtc gtc gga gcc atg gag ggg gtc       96
Pro Ala Phe Ser Pro Ala Ala Val Val Val Gly Ala Met Glu Gly Val
            20                  25                  30

tcc gtg ccc gtg act gtg ccc ccg gtc agg acg gcg tcc gcg gtg gac      144
Ser Val Pro Val Thr Val Pro Pro Val Arg Thr Ala Ser Ala Val Asp
        35                  40                  45

gac gac gcg ctg gcg ccg gga gag gaa ggg gga gac gcc tct ttg gcc      192
Asp Asp Ala Leu Ala Pro Gly Glu Glu Gly Gly Asp Ala Ser Leu Ala
    50                  55                  60

ggg agc ccg tgc tcg gtg gtc agc gac tgt agc agc gtg gcc agc gct      240
Gly Ser Pro Cys Ser Val Val Ser Asp Cys Ser Ser Val Ala Ser Ala
65                  70                  75                  80

gat ttc gag ggg gtc ggg ctg tgt ttc ttc ggc gcg gca gca ggc gcg      288
Asp Phe Glu Gly Val Gly Leu Cys Phe Phe Gly Ala Ala Ala Gly Ala
                85                  90                  95

gag ggt ggt ccc atg gtg ttg gag gac tcg acc gcg tct gca gcc acg      336
Glu Gly Gly Pro Met Val Leu Glu Asp Ser Thr Ala Ser Ala Ala Thr
            100                 105                 110

gtc gag gcg gag gcc agg gtc gcg gct ggt ggg agg agt gtc ttc gcc      384
Val Glu Ala Glu Ala Arg Val Ala Ala Gly Gly Arg Ser Val Phe Ala
        115                 120                 125

gtg gac tgc gtg ccg ctg tgg ggc tac act tcc ata tgc ggc cgc cgt      432
Val Asp Cys Val Pro Leu Trp Gly Tyr Thr Ser Ile Cys Gly Arg Arg
```

```
    130                 135                 140

ccg gag atg gag gat gcc gtt gct ata gtg ccg cga ttc ttt gac ttg      480
Pro Glu Met Glu Asp Ala Val Ala Ile Val Pro Arg Phe Phe Asp Leu
145                 150                 155                 160

cca ctc tgg ttg ctc acc ggc aat gcg atg gtc gat ggc ctc gat ccc      528
Pro Leu Trp Leu Leu Thr Gly Asn Ala Met Val Asp Gly Leu Asp Pro
                165                 170                 175

atg acg ttc cgc tta cct gca cat ttc ttt ggt gtc tat gac gga cac      576
Met Thr Phe Arg Leu Pro Ala His Phe Phe Gly Val Tyr Asp Gly His
            180                 185                 190

gat ggt gca cag gta gca aat tac tgt cgg gaa cgc ctc cat gtg gcc      624
Asp Gly Ala Gln Val Ala Asn Tyr Cys Arg Glu Arg Leu His Val Ala
        195                 200                 205

cta ctg gag cag ctg agc agg ata gag gag act gcg tgt gca gct aac      672
Leu Leu Glu Gln Leu Ser Arg Ile Glu Glu Thr Ala Cys Ala Ala Asn
    210                 215                 220

ttg gga gac atg gag ttc aag aaa cag tgg gaa aag gtc ttt gtg gat      720
Leu Gly Asp Met Glu Phe Lys Lys Gln Trp Glu Lys Val Phe Val Asp
225                 230                 235                 240

tct tat gct aga gtg gat gac gag gtt ggg gga aac acg atg agg gga      768
Ser Tyr Ala Arg Val Asp Asp Glu Val Gly Gly Asn Thr Met Arg Gly
                245                 250                 255

ggt ggt gaa gaa gca ggc aca agt gat gct gct atg aca ctc gtg cca      816
Gly Gly Glu Glu Ala Gly Thr Ser Asp Ala Ala Met Thr Leu Val Pro
            260                 265                 270

gaa cct gtg gca cct gag acg gtg ggt tcg acg gcg gtc gtc gct gtc      864
Glu Pro Val Ala Pro Glu Thr Val Gly Ser Thr Ala Val Val Ala Val
        275                 280                 285

atc tgc tcc tca cat atc att gtc tcc aac tgt gga gat tca cgg gca      912
Ile Cys Ser Ser His Ile Ile Val Ser Asn Cys Gly Asp Ser Arg Ala
    290                 295                 300

gtg ctc tgc cga ggc aag cag cct gtg cct ctg tcg gtg gat cat aaa      960
Val Leu Cys Arg Gly Lys Gln Pro Val Pro Leu Ser Val Asp His Lys
305                 310                 315                 320

cct aac agg gag gat gag tat gca agg att gag gca gag ggt ggc aag     1008
Pro Asn Arg Glu Asp Glu Tyr Ala Arg Ile Glu Ala Glu Gly Gly Lys
                325                 330                 335

gtc ata caa tgg aac ggt tat cga gtt ttc ggt gtt ctt gca atg tcg     1056
Val Ile Gln Trp Asn Gly Tyr Arg Val Phe Gly Val Leu Ala Met Ser
            340                 345                 350

cga tca att ggt gac aga tat ctg aag cca tgg ata att cca gtc cca     1104
Arg Ser Ile Gly Asp Arg Tyr Leu Lys Pro Trp Ile Ile Pro Val Pro
        355                 360                 365

gag gta aca ata gtt ccg cgg gct aag gat gac gag tgc ctt att ctt     1152
Glu Val Thr Ile Val Pro Arg Ala Lys Asp Asp Glu Cys Leu Ile Leu
    370                 375                 380

gcc agt gac ggc ctc tgg gat gta atg tca aat gaa gag gta tgt gaa     1200
Ala Ser Asp Gly Leu Trp Asp Val Met Ser Asn Glu Glu Val Cys Glu
385                 390                 395                 400

atc gct cgc aag cgg ata ctt ctg tgg cac aaa aag aac agc aca agc     1248
Ile Ala Arg Lys Arg Ile Leu Leu Trp His Lys Lys Asn Ser Thr Ser
                405                 410                 415

tca tca tca gcc cca cgg gtt ggt gac tcc gca gac tca gcc gct caa     1296
Ser Ser Ser Ala Pro Arg Val Gly Asp Ser Ala Asp Ser Ala Ala Gln
            420                 425                 430

gcg gct gct gaa tgc ttg tca aag ctt gct ctt cag aag ggg agc aaa     1344
Ala Ala Ala Glu Cys Leu Ser Lys Leu Ala Leu Gln Lys Gly Ser Lys
        435                 440                 445

gac aac att act gtc gtg gta gtt gat ctg aaa gca cag cgc aag ttc     1392
Asp Asn Ile Thr Val Val Val Val Asp Leu Lys Ala Gln Arg Lys Phe
```

```
    450                 455                 460

aag agc aaa act taa                                                     1407
Lys Ser Lys Thr  *
465


<210> SEQ ID NO 12
<211> LENGTH: 468
<212> TYPE: PRT
<213> ORGANISM: Zea mays

<400> SEQUENCE: 12

Met Glu Asp Val Val Ala Val Val Ala Ser Leu Ser Ala Pro Pro Ala
1               5                   10                  15

Pro Ala Phe Ser Pro Ala Ala Val Val Val Gly Ala Met Glu Gly Val
            20                  25                  30

Ser Val Pro Val Thr Val Pro Pro Val Arg Thr Ala Ser Ala Val Asp
        35                  40                  45

Asp Asp Ala Leu Ala Pro Gly Glu Glu Gly Gly Asp Ala Ser Leu Ala
    50                  55                  60

Gly Ser Pro Cys Ser Val Val Ser Asp Cys Ser Ser Val Ala Ser Ala
65                  70                  75                  80

Asp Phe Glu Gly Val Gly Leu Cys Phe Phe Gly Ala Ala Ala Gly Ala
                85                  90                  95

Glu Gly Gly Pro Met Val Leu Glu Asp Ser Thr Ala Ser Ala Ala Thr
            100                 105                 110

Val Glu Ala Glu Ala Arg Val Ala Ala Gly Gly Arg Ser Val Phe Ala
        115                 120                 125

Val Asp Cys Val Pro Leu Trp Gly Tyr Thr Ser Ile Cys Gly Arg Arg
    130                 135                 140

Pro Glu Met Glu Asp Ala Val Ala Ile Val Pro Arg Phe Phe Asp Leu
145                 150                 155                 160

Pro Leu Trp Leu Leu Thr Gly Asn Ala Met Val Asp Gly Leu Asp Pro
                165                 170                 175

Met Thr Phe Arg Leu Pro Ala His Phe Phe Gly Val Tyr Asp Gly His
            180                 185                 190

Asp Gly Ala Gln Val Ala Asn Tyr Cys Arg Glu Arg Leu His Val Ala
        195                 200                 205

Leu Leu Glu Gln Leu Ser Arg Ile Glu Glu Thr Ala Cys Ala Ala Asn
    210                 215                 220

Leu Gly Asp Met Glu Phe Lys Lys Gln Trp Glu Lys Val Phe Val Asp
225                 230                 235                 240

Ser Tyr Ala Arg Val Asp Asp Glu Val Gly Gly Asn Thr Met Arg Gly
                245                 250                 255

Gly Gly Glu Glu Ala Gly Thr Ser Asp Ala Ala Met Thr Leu Val Pro
            260                 265                 270

Glu Pro Val Ala Pro Glu Thr Val Gly Ser Thr Ala Val Val Ala Val
        275                 280                 285

Ile Cys Ser Ser His Ile Ile Val Ser Asn Cys Gly Asp Ser Arg Ala
    290                 295                 300

Val Leu Cys Arg Gly Lys Gln Pro Val Pro Leu Ser Val Asp His Lys
305                 310                 315                 320

Pro Asn Arg Glu Asp Glu Tyr Ala Arg Ile Glu Ala Glu Gly Gly Lys
                325                 330                 335

Val Ile Gln Trp Asn Gly Tyr Arg Val Phe Gly Val Leu Ala Met Ser
            340                 345                 350
```

```
Arg Ser Ile Gly Asp Arg Tyr Leu Lys Pro Trp Ile Ile Pro Val Pro
        355                 360                 365

Glu Val Thr Ile Val Pro Arg Ala Lys Asp Asp Glu Cys Leu Ile Leu
    370                 375                 380

Ala Ser Asp Gly Leu Trp Asp Val Met Ser Asn Glu Glu Val Cys Glu
385                 390                 395                 400

Ile Ala Arg Lys Arg Ile Leu Leu Trp His Lys Lys Asn Ser Thr Ser
                405                 410                 415

Ser Ser Ser Ala Pro Arg Val Gly Asp Ser Ala Asp Ser Ala Ala Gln
            420                 425                 430

Ala Ala Ala Glu Cys Leu Ser Lys Leu Ala Leu Gln Lys Gly Ser Lys
        435                 440                 445

Asp Asn Ile Thr Val Val Val Val Asp Leu Lys Ala Gln Arg Lys Phe
    450                 455                 460

Lys Ser Lys Thr
465


<210> SEQ ID NO 13
<211> LENGTH: 8861
<212> TYPE: DNA
<213> ORGANISM: Zea mays
<220> FEATURE:
<221> NAME/KEY: exon
<222> LOCATION: (3216)...(3677)
<220> FEATURE:
<221> NAME/KEY: exon
<222> LOCATION: (3775)...(4083)
<220> FEATURE:
<221> NAME/KEY: exon
<222> LOCATION: (4200)...(4310)
<220> FEATURE:
<221> NAME/KEY: exon
<222> LOCATION: (4388)...(4744)
<220> FEATURE:
<221> NAME/KEY: 5'UTR
<222> LOCATION: (3027)...(3215)
<220> FEATURE:
<221> NAME/KEY: promoter
<222> LOCATION: (1)...(2986)

<400> SEQUENCE: 13

atgctgggga acttgggatc taacctgcaa ggtgactcaa cttaaggctt gttcggttag      60

ctcttaatcc atgtggattg agtgagattg ggtgggttta aatccaaagc aagttaaatt     120

tcttcataat tttttcgaat cccgtccaat gcatagataa agggattaac cgaacaaggc     180

ctgatggaga tatagaaaga cctctgatgg gactaatgct cttgacaatc ccaatttcag     240

caggacattt gctttctcgt tttttttct tctcaaagtg tatgcaaaaa ctcaatacta      300

tcaaatccat tttgagttca aagcacgagc aagggaggct ttgatccttg acaatactcg     360

tcactcaggt atggaaggag agaaacaaca tgttatatag ttaagcagac tgaatccaca     420

aactatagcg ttatgcacaa cattaaatac agtatgaggc aggcttttga tcacaacgga     480

agcaaaacag ctttctcgtc tctttcatct tgattgaact gagattttta ttttactttt     540

aaggctgagg tcttgagctt cattgttgtt tagttttgtt ctatgcttca gttgtgcctg     600

tacagtaccc atctatattt aactttctta tttttaatat cgtgggcagc tctgtccgtc     660

tcgtttgaga aatagatgat ccacataaaa attgaaattt ggtgcttaat gtgctctttt     720

ttctttcttt ctttctcttt tgtaccatat tctttctttg ttttgttttt ctctgtcttt     780

tcctcctggg tttagtcctc acgttttgca ttagaatttc tctctaataa tttaatgttc     840

aagtgtggat atctactttt gctttatagc atcctcgtaa acacataatg ctatcttaaa     900
```

-continued

```
atagcggtgt cgtggttttg gaaaccgaga gacaatatat tcgtgctatc ttaaaataga    960
aatttcttgg aaaaatggga tttccaaatt agctcttaga attgagaaac tgattgagat   1020
aaagacatgc caatatgtgg agaatgagaa aagaggttgg gtagcactca gcgagatgtt   1080
tgctcatacg tttggttcca gttgtccatc agaaatgaag gcacaagcat aagggcggtg   1140
ttttcctcta tggatcggaa actaaacaga gttcctagta gagaaagcaa gaggtaaggc   1200
agtcctgcat cgtcagttcg ccactgatag tgattttcaa gggcgtcagc catgttcttt   1260
tcaggccaaa attcttctcc agcgttcgtc ccctttgtcc acacgtcacg ccgttgccgc   1320
atgatggcag ttgtttcttt caagcagagt ggcatcgatt gcatgtagga gtatactgta   1380
tacatgcatg acggagtagg tgtgtttttt agttctctgc gtgcaagcct gaaagagcga   1440
ggaaacgttt accacgccag agacgccacc aagaaattga cttgtacgac ttgcaaacgg   1500
gcatcataaa caggtaacgc gctacgacat atactcgcat acgtggtgca tctacacaac   1560
agtcccgcac ccgataatga aatgagagta attttatcga cgcgcattga gagcttattt   1620
ggatactcta ttattcatcc aaatacacat gagttaaaga caattgaggc gtaaattaaa   1680
ctaatttata tataatctat ctcaaaccat atgtatcgtg gtgaataata gactcttcaa   1740
acatagccgg ctgatctgat ttcacccgct ttcattgtca tgcttgccat atcatagcaa   1800
atccgaagcg agcacgaaaa gaatggcgat cactgtggtt gcagccctta cacaggctgc   1860
tttaccactt cactgacaga ccgcaggtac tacctgctgc agcgaccact ctattaccag   1920
tacgtacctg gtagtacgta catgcgccga gctactgtgt acggttacca accaaaatga   1980
cgcgtgttcg cggcgccgtg gaagtgcgcg ccggcccgag tttcccccat accgaaccga   2040
gccgacgagc ggtgactcag catgcaccag ctgcccccca ttcggcgcct gcccgcatgc   2100
agtgcaccgg gccaccgccg ctcggcactg gcaggcacca gcaagcccgc aacgtgcggc   2160
acaccgcaca ccggactgtc agccgcggcc ggccgcgccc cctgcatctt gcagcggcag   2220
ttctctcatc tctgcacggc gtggctccta tctgcgtgcg cctcgctttt tcccaggttc   2280
acctcccctc gcccccatcg tggccacgcc agcgcccaac caccgctcgc cggcccgcct   2340
ccccccacgc aagccctgta cacgtgtcca ccggtaccgc gaccgaccac cttcccactg   2400
attgcgaccg ccccaaccac gtgtcccttc tccatcacta cacccgttcc ctcgtgctcc   2460
cgccctgaga ctctctttct cgctggcagg tgggcgacgc ttcagccagt ccccacatgt   2520
catcgaatcc tgaacaaaga gcggtaggga agagtacgta ctactgtgga gtccggatat   2580
ttttctgggc agcccgagag acagaaccca tgtggtgggg accgcaatag taggcatcaa   2640
taaatcagct gccgaggcgg actgccccac ccaccccagg agcgccacgt gtgtgcagca   2700
cagggattag gcgataaaca caccatcaaa cttcctcgtg ggcccgcacc tcgcccgcct   2760
cggtggccga tgcacaccac gtgtcgatcg cgctgagcaa gataccggca cgcgtccgga   2820
tcctgccggg acggacggcc ccggtgcgcc ggaccaggag cacgtcgcaa cagctgtacg   2880
tgtcgaggcg ctgcccgtga cggcgacggc ccccctgccc ggctgcccct gcccgcctcg   2940
cctcgcctct cttgtactgc ccccacgaag cattcgtgct cgtttcgcct cgcgcccgcg   3000
ctgctgtcct gctgctgcta ttttgccatt gcatccattt ccgggggacg gagtggagga   3060
ggagggcgtc gcctgcgttg cttcgcgtgg gaagcgtagc gtgcttcgtt taggcctctc   3120
gccaatatcc gagggttaat ctagagaggc ctttggcttt gccagacgcg cctgtacgcg   3180
cctttctggg aggcagccgc ttgctctcgc ctccaatggc cgagatctgc tgcgaagaag   3240
ccaagtccac gccggcgacc gccgtggctg cggcttcagt ctccgccacg gccgctgcgg   3300
```

-continued

```
ccgccgccgt ggcagtggcc tcctcggcgt tagagaggag gcgacgcagg ttggagatga   3360
ggaggttccg cgtcgcgggc gatcccgagg cgccggtcgc ggaggacgtc cgcgccgcca   3420
agcggcagag gctggcgcgc acgctgtcca gcacctgccc cgacgcgggc tcaggctcgg   3480
gctcggactc cgacaggcct gccctaccgg agcggttgcc caggtacggg gtcacctccg   3540
tctgcggccg acgccgcgag atggaggaca cggtctccgt taggccggac tttgtgcccg   3600
gcaccagcaa acagcacttc ttcggcgtct tcgacggcca cggctgctcc cacgtacgcc   3660
atactcgtac acgacgcgcg cgcatctagg agtttaaatc ccttttgcgg agttctgtat   3720
gctgatcgca gtttcgcgct tttgctgtag gtagcaacca tgtgccagaa catgatgcac   3780
gaggtggtcg cggacgagca caggaaggca gattgttctg gcgaagagac ggcgtggaag   3840
gccgtgatgg agaggagctt cgcgcgactg gacgagcagg ccgccagctg ggcgaccagc   3900
cgcagccgcg acgagccctc ctgcaggtgc gagcagcaga agcccttgcg ttgcgatcac   3960
gtggggtcca ccgccgtggt cgccgtcgtc agccccaccc acgttgtcgt cgccaacgcc   4020
ggcgactccc gcgccgtcct atcccgcgcc ggcgtccccg ttccgctgtc cgtcgaccac   4080
aaggtctgta tactcgtgca tcacggggct gagggcgctg cgcctcctcc cctgtcccct   4140
ccccgcgtct tcgtcgcctg tccgtgagcc tgacgtgctc aacttcctga ttcgttcagc   4200
ctgaccggcc tgacgagctg gcgcgcatca aggcggcggg cggccgcgtc atttactggg   4260
acggtgctcg tgttctcggc gtcctcgcca tgtctcgagc cataggtgag ctgggctcat   4320
tcggggtcgt tttgggtcca ctcgttggac ttgaactgac gggtttatgc gcgcgcgtgc   4380
aggcgacgga tacctgaagc cgttcgtgtc gtcggagccg gaggtaacgg tgacggagcg   4440
caccgacgac gacgagtgcc tgatcctggc cagcgacggc ctgtgggacg tcgtgaccaa   4500
cgagatggcg tgcgaggtcg tccgcgcgtg cttccacagc aacggtccgc cggcgccggc   4560
cgctcgggcg aacggcgcgg ccctccgggc agccgagaac ggatccgcgg ccgccaaggg   4620
cgtgagcgtg gaggattccg acaaggcgtg ctccgacgcg gccatgctgc tggcgaagct   4680
ggcgctggcc cggcggagcg ccgataatgt tagcgtggtc gtcgtggatc tccgccgggg   4740
gatatgattt gccttccttc ctttttagcc ctcttggaat ccaagctaat ttctccccg    4800
ttttcttcca tacttttagg ttctgttttg gtttagtatt aatactgtag tagttaccaa   4860
ccagacgctt ttcttctctc aaacgaggaa ttaaaagcca gtcggaccaa ggaaatagaa   4920
catcgaattg cacacagatg cacaaggtag tggtaatcgt taatcatagc tttttttggc   4980
cgtcgattaa cgcgctaaaa agtgctgatt ccattctttg actgaagtag attaacgggg   5040
cgattggtgt agaaattggc gctaagacca cgtttagcgg gagcagattg cgattggttg   5100
gcccaggcag gcggtaggat tcggagacgg attaacaaag gcacggcaag atgctgatct   5160
atctgtgggg tgtgggcccg tcgtctatcg agtgaaggga aatgctccga agttctcgtt   5220
tacggaaatg agaaacgggc atctttccac aggggcggcc tgggcctgaa tgatgcgacg   5280
acccacgatc aatggttacc tttcgcccgc ggcgtcgtgc gtgggcggcg aggcgacaga   5340
gcatttgcct ttgtccgact gtccgttggg cgatcgaccg gtcgggtcag gcgctgttga   5400
agccattatc gaggcctgcg ccgcgccttt tggtactcct ctggagtctg gagtgctacg   5460
gcggggcgcg ccgctcgcac atggcgcggc tggttgacag gagctgggtg ttccggggtg   5520
tcggagaccc cgtagcgtag cacggtgcca tggtcggcga gtgactgtgt tcaattattg   5580
gttgatgccc gtatccgtta cgcgtcctcc cgcaccgtgc cggcgggccg catgccaagc   5640
tcccacgaat atcggcggtt gccgttggcg caggggcaag gcgagccgcc ggggagggag   5700
```

-continued

```
ttatggagac gcaaacgcaa cagcccctct ctccggtagt tcggtcgtcc cacgaagtgc   5760
cgggcacgtc tgggctgggc cggcgagccg gctgtagaat tgacacaaca gcgagcgcgt   5820
ccccgtcgga gatctagcaa gggaagatat cccatgatat gtgcggctat gggctatcgg   5880
tctactccat ctcgaaggaa ctgtgacggg aaagagagga gagccatcga ctatcgtgct   5940
atcgaaaagc ggcggacctt gaacgctcct ggcgttgctg catgctcttt tgcagcatgc   6000
catccgagcg tccgctcccg tccacatcca atcctttagg acgcgtttaa aaaacaaagt   6060
aaattttata gtttttaggc aatattctgg tttataaaaa tactgtagta tttttgtacc   6120
ataaaatgtt ttactgtatt cttttaaaaa aacattttca aacccagcat ttccagggta   6180
atttcgttcc atattttagt cttcactttt gtaattagtt ttataactag actatattta   6240
atactcatta ttgaaattca aatatccgac aacgtaggag gcgaaccttg agccgatgca   6300
tccgagttgg tagggcgacg tggtccaatg gtgaggagtt caactgcgga gaataggttt   6360
ggtcatttgg cagcgcgttg aagcagcctc ctcgatgtgt gggggacagg gggagtgacg   6420
atccgacgac gaagaagctt gtgtcacgcc taccttgata tgcaggaaaa gagagaaaaa   6480
agagcacgcc aggtcgagct atctcgctgc gccggaaagg ggggaaaaat gagcatgcgg   6540
tgtgaagaaa acaacgccaa accgttttta gagtgtcgat cgatttgaca aatctagaaa   6600
gcaaatgagg ttgaatagca agttactaaa tttaataagt ttatttggag aactattgaa   6660
gaagcatttt tttcatttct aaatttaaaa tttaggtaat tatttagaaa accattgaaa   6720
ttgctctaga ctttaattag gaaagcaaac accggaaaag tctgacagct caaaagaaga   6780
gaggtagggc tcgagggaaa atggctatgg acgaaaacga gaaaatattg aatattagat   6840
gtacatatag attaggggta cttatattag catgactgtt gaattttgtg gccccgacta   6900
tagatggcaa tggatacccg aaatctaaat acccaacggg ctttatccga tatgaaggtg   6960
ggtacgagat gatttctcta cccacgggta tgttaataag caagaatttc tatctgttgg   7020
gtagacgggt atgggttggt attacccata cctgtctacc tataggtaaa atatactcgt   7080
atcaatgcct tggccatgga ggacctaatc atcaaagtct ccacagtaac ctacatacca   7140
tgaaggacat gaccatacac cataccaggt gtatgcctac gtatgacgga gggtgatgca   7200
gggttcatga cgaaagacaa gactgcatcg cgcacggcct cgcacacata ccatgagtct   7260
acctcgtggg acccatcagg cgtcagtaca aggacatcag catcgaactc gctataggga   7320
cctgtatacc agacgaaaag aaccagtacg tcatgccggg gatacagctg cacacgacct   7380
atggatgatg tcagagggac tacgtcaact gatcacactc ttagcagtag gaagcaagta   7440
gcaagtctac tctgtaaggt cctacccttg agctataaat ggataggccc cttccttctt   7500
tccacacacg caccaactgt aataacagtc ctcaagcaat actacgatca acattgcaat   7560
gaactagggc gaaagcctga accagtataa ctctctatct caaacccttt gctcgaagcc   7620
ctggtggttc accattcgga gtgagtccgc gctagcatcc cttgtcgaac acaaattcta   7680
ttgtcctctg gtttccgaaa ccaaaacagg ttgcatggac gcttgcacgt cccctagaag   7740
tttccgatga aaaccttctc catactggcg cacccctgga tgcatccttc ttgcaggtac   7800
tcgggccaag cttgagccga ctccactaga tagatgggaa ggtattgtat gatcatcatg   7860
tcgtcccttg ctcctctcat gtaggaagcg aggcggtaca ccttgagcta aacagatggt   7920
tttttggtc ttgtcatatt ttgtgatgtt ggttagagac cgaaactgtc aggaaaactc   7980
tatggtgtgg atggcctatc caaataccca agccccaagt gagccttcct gcttttgtgg   8040
ttgttgccat gttggggctt aggcctcgag ctagcttgac ctgctcttgg gcgaggtgac   8100
```

-continued

```
tcgtgttgag gattacacgc atgtcgtgta cccttcccaa gtgttatcac accagggcac   8160

atgacatcta gggttgttgg gtcacttctt tgtaggcccg gtcttgggga tgggcattga   8220

taacctttgt tcgctggctg actccattta ggtagaggcg gctgaaaggg aaatagacgt   8280

aaaccatttt tctatattga ttttggtgct agatggccat cacaaccttt cgaactaact   8340

agtttttcta cgctttgatt cacagattca taagtccaat aattcagttc caaagtgaga   8400

aacaactcaa aaccaagaaa aaaggggtaa tacttggaat agattatcta gtagtagttc   8460

tacactttgg ataagttcta aattccccta ggaacctttt tgacctatct agaagggttg   8520

gaaagctcag attcaacgaa acacactttt ggagctagtt tgagctaaag caagcactat   8580

gagtaagaca aattgcgctc tccaaattct gtgacttaaa ctagttggat agtctctaga   8640

tatgtttgta taagtaataa gaacattctt aagcgcagcc aaatcaaatt agataaaaaa   8700

atagacaagt ttgccaaatt tggtttgagt ctgaaagcac tggatcggtc tagtggctca   8760

tcgggcctct tacgtaggga aggttcagac ttgtccttgg cggcagtcag accaaaccag   8820

tctagtgacg catcggactg cttacgcaga gaggattaaa a                       8861
```